US012776389B2

(12) United States Patent
Eberle

(10) Patent No.: US 12,776,389 B2
(45) Date of Patent: Oct. 27, 2026

(54) GRAPH REFERENCE GENOME AND BASE-CALLING APPROACH USING IMPUTED HAPLOTYPES

(71) Applicant: Illumina, Inc., San Diego, CA (US)

(72) Inventor: Michael A Eberle, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 1027 days.

(21) Appl. No.: 17/817,917

(22) Filed: Aug. 5, 2022

(65) Prior Publication Data

US 2023/0095961 A1 Mar. 30, 2023

Related U.S. Application Data

(60) Provisional application No. 63/246,626, filed on Sep. 21, 2021.

(51) Int. Cl.
*G16B 20/20* (2019.01)
*G16B 45/00* (2019.01)

(52) U.S. Cl.
CPC ............. *G16B 20/20* (2019.02); *G16B 45/00* (2019.02)

(58) Field of Classification Search
CPC ........ G16B 20/20; G16B 45/00; G16B 30/10; G16B 40/20
See application file for complete search history.

(56) References Cited

U.S. PATENT DOCUMENTS

| | | | | |
|---|---|---|---|---|
| 10,354,747 | B1 * | 7/2019 | DePristo | G06F 18/22 |
| 12,573,472 | B2 * | 3/2026 | Hernandez | G16B 20/20 |
| 2018/0039730 | A1 * | 2/2018 | Browning | G16B 30/00 |

(Continued)

FOREIGN PATENT DOCUMENTS

WO WO-2021072037 A1 * 4/2021 ............. G16B 30/10

OTHER PUBLICATIONS

Larmer SG, Sargolzaei M, Brito LF, Ventura RV, Schenkel FS. Novel methods for genotype imputation to whole-genome sequence and a simple linear model to predict imputation accuracy. BMC Genet. Dec. 27, 2017;18(1):120. doi: 10.1186/s12863-017-0588-1. PMID: 29281958; PMCID: PMC5746022. (Year: 2017).*

(Continued)

*Primary Examiner* — Sun M Li

(74) *Attorney, Agent, or Firm* — Keller Preece PLLC

(57) ABSTRACT

The present disclosure relates to systems, non-transitory computer-readable media, and methods for generating a graph reference genome customized for a particular sample genome and utilizing the customized graph reference genome to determine final nucleotide-base calls for the sample genome. To illustrate, the disclosed systems can generate a customized graph reference genome including various paths representing imputed haplotypes corresponding to a particular genomic region. Additionally, or alternatively, the disclosed system can determine and compare direct and imputed nucleotide-base calls for a sample genome as a basis for generating final nucleotide-base calls. In some such cases, the disclosed system weights (and selects between) direct nucleotide-base calls and imputed nucleotide-base calls for genomic coordinates based on sequencing metrics corresponding to the direct nucleotide-base calls or based on the variability of the genomic regions comprising the genomic coordinates.

20 Claims, 15 Drawing Sheets

(56) References Cited

U.S. PATENT DOCUMENTS

| | | | | |
|---|---|---|---|---|
| 2019/0026433 | A1* | 1/2019 | Lu | G06F 16/13 |
| 2019/0026641 | A1* | 1/2019 | Lu | G16B 30/00 |
| 2021/0065847 | A1* | 3/2021 | Valouev | G16B 40/00 |
| 2021/0174901 | A1* | 6/2021 | Ashutosh | G16B 20/00 |
| 2023/0368864 | A1* | 11/2023 | Nemri | G16B 20/00 |
| 2024/0112753 | A1* | 4/2024 | Andrews | G16B 20/20 |

OTHER PUBLICATIONS

Fridley BL, Jenkins G, Deyo-Svendsen ME, Hebbring S, Freimuth R. Utilizing genotype imputation for the augmentation of sequence data. PLoS One. Jun. 8, 2010;5(6):e11018. doi: 10.1371/journal.pone.0011018. PMID: 20543988; PMCID: PMC2882389. (Year: 2010).*

Nelson SC, Doheny KF, Pugh EW, Romm JM, Ling H, Laurie CA, Browning SR, Weir BS, Laurie CC. Imputation-based genomic coverage assessments of current human genotyping arrays. G3 (Bethesda). Oct. 3, 2013;3(10):1795-807. doi: 10.1534/g3.113.007161. PMID: 23979933; PMCID: PMC3789804. (Year: 2013).*

Dolled-Filhart MP, Lee M Jr, Ou-Yang CW, Haraksingh RR, Lin JC. Computational and bioinformatics frameworks for next-generation whole exome and genome sequencing. ScientificWorldJournal. 2013;2013:730210. doi: 10.1155/2013/730210. Epub Jan. 13, 2013. PMID: 23365548; PMCID: PMC3556895. (Year: 2013).*

Sona P, Hong JH, Lee S, Kim BJ, Hong WY, Jung J, Kim HN, Kim HL, Christopher D, Herviou L, Im YH, Lee KY, Kim TS, Jung J. Integrated genome sizing (IGS) approach for the parallelization of whole genome analysis. BMC Bioinformatics. Dec. 3, 2018;19(1):462. doi: 10.1186/s12859-018-2499-1. MID: 30509173; P (Year: 2018).*

Jensen Sarah E. et al: "A sorghum practical haplotype graph facilitates genome-wide imputation and cost-effective genomic prediction", The Plant Genome, vol. 13, No. 1, Mar. 1, 2020 (Mar. 1, 2020), XP093038144, USA ISSN: 1940-3372, DOI: 10.1002/tpg2.20009 Retrieved from the Internet: URL: https://onlinelibrary.wiley.com/doi/full-xml/10.1002/tpg2.20009.

Rakocevic Goran etal; "Fast and accurate genomic analyses using genome graphs", Nature Genetics, Nature Publishing Group US, New York, vol. 51, No. 2, Jan. 14, 2019 (Jan. 14, 2019), pp. 354-362, XP036688482, ISSN: 1061-4036, DOI: 10.1038/S41588-018-0316-4 [retrieved on Jan. 14, 2019]; &Rakocevic Goran et al: "Fast and accurate genomic analyses using genome graphs—Supplementary Material". Nature Genetics, vol. 51, No. 2, Jan. 14, 2019 (Jan. 14, 2019), pp. 354-362, XP055933375, New York; ISSN: 1061-4036, DOI: 10.1038/s41588-018-0316-4; Retrieved from the Internet: URL:http://www.nature.com/articles/s41588-018-0316-4.pdf.

Shi, Shuo et al. "Comprehensive Assessment of Genotype Imputation Performance"; Human Heredity; Published online: Jan. 22, 2019; https://www.karger.com/Article/Pdf/489758.

Paten B, Novak AM, Eizenga JM, Garrison E. Genome graphs and the evolution of genome inference. Genome Res. May 2017;27(5):665-676. doi: 10.1101/gr.214155.116. Epub Mar. 30, 2017. PMID: 28360232; PMCID: PMC5411762.

Ameur, A. Goodbye reference, hello genome graphs. Nat Biotechnol 37, 866-868 (2019). https://doi.org/10.1038/s41587-019-0199-7.

Committee Opinion, Committee on Genetics, The American College of Obstetricians and Gynecologists, Carrier Screening for Genetic Conditions [online]. No. 691, Mar. 2017 (Reaffirmed 2020) [retrieved on May 23, 2024]. Retrieved from the internet: <URL: https://www.acog.org/clinical/clinical-guidance/committee-opinion/articles/2017/03/carrier-screening-for-genetic-conditions#:~:text=The%20Tay%E2%80%93Sachs,on%20the%20panel>Tay-Sachs Disease, p. 13.

Course MM, Gudsnuk K, Smukowski SN, Winston K, Desai N, Ross JP, et al. "Evolution of a Human-Specific Tandem Repeat Associated with ALS", American Journal of Human Genetics, Sep. 3, 2020; 107(3): 445-460. doi: 10.1016/j.ajhg.2020.07.004. Epub Aug. 3, 2020. Retrieved from webpage: <https://www.ncbi.nlm.nih.gov/pmc/articles/PMC7477013/>.

CYP21A2 cytochrome P450 family 21 subfamily A member 2 [*Homo sapiens* (human)], webpage <URL: https://www.ncbi.nlm.nih.gov/gene?Db=gene&Cmd=DetailsSearch&Term=1589> NIH, National Library of Medicine, National Center for Biotechnology Information, Gene ID: 1559, 9 pages, May 18, 2023, retrieved from Internet Archive Wayback Machine <URL: https://web.archive.org/web/20230613052706/https://www.ncbi.nlm.nih.gov/gene?Db=gene&Cmd=DetailsSearch&Term=1589> on May 23, 2024.

Database of Bioinformatics Software Tools and Resource. "SHAPEIT (Segmented HAPlotype Estimation and Imputation Tool)", webpage: <URL: https://bioinformaticshome.com/tools/imputation/descriptions/SHAPEIT.html#gsc.tab=0> 1 page, Dec. 8, 2022, retrieved from Internet Archive Wayback Machine <https://web.archive.org/web/20221208161351/https://bioinformaticshome.com/tools/imputation/descriptions/SHAPEIT.html#gsc.tab=0> on May 22, 2024.

Dragen DNA Pipeline—Repeat Expansion Detection with Expansion Hunter. Illumina, 2 pages, [online], [retrieved on May 23, 2024]. Retrieved from the Internet: <URL: https://support.illumina.com/content/dam/illumina-support/help/Illumina_DRAGEN_Bio_IT_Platform_v3_7_1000000141465/Content/SW/RepeatGenotyping_fDG_dtSW.htm>.

G. Emilien, M. Ponchon, C. Caldas, O. Isacson, J.-M. Maloteaux, "Impact of genomics on drug discovery and clinical medicine", QJM: An International Journal of Medicine, vol. 93, Issue 7, Jul. 1, 2000, pp. 391-423. Retrieved from webpage: <https://doi.org/10.1093/qjmed/93.7.391>.

Hehir-Kwa Jayne Y. et al. "A high-quality human reference panel reveals the complexity and distribution of genomic structural variants", Nature Communications, [Online] vol. 7, No. 1, Oct. 6, 2016 (Oct. 6, 2016), XP093122719, UK ISSN: 2041-1723, DOI: 10.1038/ncomms129889.

Hoffmann Thomas J. et al. "Strategies for Imputing and Analyzing Rare Variants in Association Studies", Trends in Genetics., vol. 31, No. 10, Oct. 6, 2015 (Oct. 6, 2015), pp. 556-563, XP093122750, NL ISSN: 0168-9525, DOI:10.1016/j.tig.2015.07.006.

Huang Jie et al. "Improved imputation of 1-25 low-frequency and rare variants using the UKIOK haplotype reference panel", Nature Communications, [Online] vol. 6, No. 1, Sep. 14, 2015 (Sep. 14, 2015), XP093122715, UK ISSN: 2041-1723, DOI: 10.1038/ncoms9111.

Kato D, Kawanishi C, Kishida I, Furuno T, Suzuki K, Onishi H, Hirayasu Y. "Effects of CYP2D6 polymorphisms on neuroleptic malignant syndrome," European Journal of Clinical Pharmacology, (2007) 63(11), 991-996. doi: 10.1007/s00228-007-0355-8. Epub Aug. 14, 2007. Retrieved from webpage: <https://pubmed.ncbi.nlm.nih.gov/17701031/>.

Moura-Massari VO, Cunha FS, Garcia Gomes L, Bugano Diniz Gomes D, Marcondes JAM, Madureira G, et al. "The Presence of Clitoromegaly in the Nonclassical Form of 21Hydroxylase Deficiency Could Be Partially Modulated by the CAG Polymorphic Tract of the Androgen Receptor Gene", PLoS One. Feb. 5, 2016, 11(2): e0148548. (2016) doi:10.1371/journal.pone.0148548. retrieved from webpage <https://pubmed.ncbi.nlm.nih.gov/26848581/>.

Repeat Expansion Detection with Expansion Hunter. Illumina, BaseSpace, Dragen Germline Online Help, 2017, 2 pages, [online], [retrieved on May 22, 2024]. Retrieved from the Internet: <URL:https://support.illumina.com/help/DRAGEN_Germline_OLH_1000000083701/Content/Source/Informatics/Dragen/RepeatGenotyping_fDG_dtSW1.htm>.

RFC1 replication factor C subunit 1 [*Homo sapiens* (human)], webpage <URL: https://www.ncbi.nlm.nih.gov/gene/5981>, NIH, National Library of Medicine, National Center for Biotechnology Information, Gene ID: 5981, 9 pages, Sep. 6, 2022, retrieved from Internet Archive Wayback Machine <URL: https://web.archive.org/web/20220927092829/https://www.ncbi.nlm.nih.gov/gene/5981> on May 23, 2024.

Science Direct. "Linkage Disequilibrium", webpage <https://www.sciencedirect.com/topics/neuroscience/linkage-disequilibrium#featured-authors>, 8 pages, Jun. 16, 2022, retrieved from Internet Archive Wayback Machine <https://web.archive.org/web/20220616161037/

(56) References Cited

OTHER PUBLICATIONS https://www.sciencedirect.com/topics/neuroscience/linkage-disequilibrium> on May 23, 2024.

Screen capture from YouTube video entitled "What is Genome Phasing?", 3 pages, uploaded on Jul. 23, 2013 by user "Illumina", Retrieved from the Internet: <URL:https://www.youtube.com/watch?v=15NPZCGP_e4>.

Sequencing 101: ploidy, haplotypes, and phasing—how to get more from your sequencing data. PacBio, Sequencing 101, Dec. 10, 2010, 10 pages, [online], [retrieved on May 21, 2024]. Retrieved from the internet <URL: https://www.pacb.com/blog/ploidy-haplotypes-and-phasing/#:~: text=Both%20trio%20and%20population%20phasing,complete%20picture%20of%20genetic%20variation>.

Sickle Cell Disease (SDC), "Data and Statistics on Sickle Cell Disease", CDC, webpage <URL:https://www.cdc.gov/ncbddd/sicklecell/data.html>, 2 pages, May 2, 2022, retrieved from Internet Archive Wayback Machine <URL: https://web.archive.org/web/20220925220602/https://www.cdc.gov/ncbddd/sicklecell/data.html> on May 23, 2024.

Tian X, Browning BL, Browning SR. "Estimating the Genome-wide Mutation Rate with Three-Way Identity by Descent", American Journal Human Genetics, 105(5), 883-893, Nov. 7, 2019; doi: 10.1016/j.ajhg.2019.09.012. Epub Oct. 3, 2019. Retrieved from webpage: <https://www.ncbi.nlm.nih.gov/pmc/articles/PMC6848988/>.

Yang Y, Botton MR, Scott ER, Scott SA. "Sequencing the CYP2D6 gene: from variant allele discovery to clinical pharmacogenetic testing", Pharmacogenomics. May 2017; 18(7):673-685. doi: 10.2217/pgs-2017-0033. Epub May 4, 2017. Retrieved from webpage: <https://www.ncbi.nlm.nih.gov/pmc/articles/PMC5591463/>.

Eric C. Anderson: "Chapter 22 Basic Handling of VCF files I Practical Computing and Bioinformatics for Conservation and Evolutionary Genomics", Nov. 7, 2020 (Nov. 7, 2020), XP093203245, Retrieved from the Internet: URL:https://web.archive.org/web/20201107212051 /https://eriqande.github.io/eca-bioinf-handbook/basic-handling-of-vcffiles.html.

* cited by examiner

GRAPH REFERENCE GENOME AND BASE-CALLING APPROACH USING IMPUTED HAPLOTYPES

CROSS-REFERENCE TO RELATED APPLICATIONS

This application claims the benefit of, and priority to, U.S. Provisional Application No. 63/246,626, entitled "A GRAPH REFERENCE GENOME AND BASE-CALLING APPROACH USING IMPUTED HAPLOTYPES," filed Sep. 21, 2021, the contents of which are hereby incorporated by reference in their entirety.

BACKGROUND

In recent years, biotechnology firms and research institutions have improved hardware and software platforms to determine a sequence of nucleotide bases (or whole genome) and identify variant calls for nucleotide bases that differ from reference bases of a reference genome. For instance, some existing nucleic-acid-sequencing platforms determine individual nucleotide bases within sequences by using existing Sanger sequencing or by using sequencing-by-synthesis (SBS). When using SBS, existing platforms can monitor tens of thousands or more oligonucleotides being synthesized in parallel to detect more accurate nucleotide-base calls from a larger base-call dataset. For instance, a camera in SBS platforms can capture images of irradiated fluorescent tags from nucleotide-bases incorporated into to such oligonucleotides. After capturing such images, existing SBS platforms send base-call data (or image data) to a computing device with sequencing-data-analysis software that aligns nucleotide reads with a reference genome. Based on the aligned nucleotide-fragment reads, existing SBS platforms can determine nucleotide-base calls for genomic regions and identify variants within a sample's nucleic-acid sequence.

Despite these recent advances, existing nucleotide-base-sequencing platforms and sequencing-data-analysis software (together and hereinafter, existing sequencing systems) sometimes inaccurately determine base calls, especially for bases in difficult-to-call genomic regions. Such difficult-to-call genomic regions may include genomic regions that historically (or for a given sample) include nucleotide reads that frequently fail to align well with a linear reference genome or produce nucleotide-base calls that exhibit low-quality sequencing metrics, such as base-call-quality and mapping quality scores below normal thresholds. For instance, existing sequencing systems frequently generate inaccurate mappings or inaccurate nucleotide-base calls for genomic regions including uncommon variants or high variability, such as a variable number tandem repeat (VNTR) region. Despite decades of failing to produce accurate nucleotide-base calls in difficult-to-call regions, existing sequencing systems frequently limit input data for a variant caller or other sequencing-data-analysis software to (i) direct nucleotide-base calls from reads compared to a linear reference genome and (ii) sequencing metrics corresponding to such direct nucleotide-base calls.

While some existing sequencing systems attempt to cure alignment-accuracy and base-calling-accuracy problems with graph reference genomes, existing graph reference genomes often include excessive alternative paths for alleles similar enough (or irrelevant) to the alleles exhibited by many sample genomes. For example, some existing sequencing systems utilize generic graph genomes that include large numbers of alternate genomic sequences and paths for alleles that are both common and uncommon across populations. Because such alternate sequences and paths can be similar to—but not match—many sample genomes' alleles, generic graph genomes frequently cause existing sequencing systems to misalign or miss call variants for a large number of samples. By utilizing generic graph reference genomes, therefore, existing sequencing systems can increase the chances of mismatched alignments with reads from a genomic sample.

In addition to alignment-accuracy problems, existing graph reference genomes are often bulky and consume considerable memory and computing resources. Indeed, some existing graph reference genomes can include countless alternative paths for alternative genomic sequences that are irrelevant to a given genomic sample. These countless alternative paths can consume unnecessary memory. In addition to wasting memory, generic graph reference genomes often increase the computer processing time for existing sequencing systems to determine whether to include or exclude matches to alternative sequences when making nucleotide-base calls.

BRIEF SUMMARY

This disclosure describes embodiments of methods, non-transitory computer readable media, and systems that can solve one or more of the foregoing (or other problems) in the art. In particular, the disclosed systems can generate a graph reference genome customized for a specific sample genome and utilize the customized graph reference genome to determine nucleotide-base calls for the sample genome. For example, the disclosed systems can determine variant nucleotide-base calls (e.g., single nucleotide polymorphisms) surrounding a genomic region of a sample genome and impute haplotypes corresponding to the genomic region based on the variant nucleotide-base calls. The disclosed systems can subsequently generate a graph reference genome for the sample genome that includes paths representing the imputed haplotypes. Based on comparing nucleotide-fragment reads of the sample genome with paths representing imputed haplotypes for the genomic region, the disclosed systems can determine nucleotide-base calls within the genomic region.

In addition or in the alternative to a sample-customized graph genome, in one or more embodiments, the disclosed systems determine and compare direct and imputed nucleotide-base calls for a sample genome as a basis for generating final nucleotide-base calls. For example, the disclosed systems can determine direct nucleotide-base calls (and corresponding sequencing metrics) based on nucleotide-fragment reads aligned with a linear or graph reference genome. Such direct nucleotide-base calls may include variant-nucleotide-base calls surrounding a genomic region. Based on such variant-nucleotide-base calls, the disclosed systems can impute haplotypes for the genomic region and determine imputed nucleotide-base calls based on imputed haplotypes. Based on the direct nucleotide-base calls, the corresponding sequencing metrics, and the imputed nucleotide-base calls, the disclosed systems determine final nucleotide-base calls for the sample genome with respect to a reference genome. For instance, the disclosed systems can utilize a weighted model (e.g., a base-call-machine-learning model) to assign weights to both direct and imputed nucleotide-base calls to determine final nucleotide-base calls for the sample genome.

Additional features and advantages of one or more embodiments of the present disclosure are outlined in the description which follows, and in part will be obvious from the description, or may be learned by the practice of such example embodiments.

BRIEF DESCRIPTION OF THE DRAWINGS

The detailed description provides one or more embodiments with additional specificity and detail through the use of the accompanying drawings, as briefly described below.

DETAILED DESCRIPTION

Figure 1:
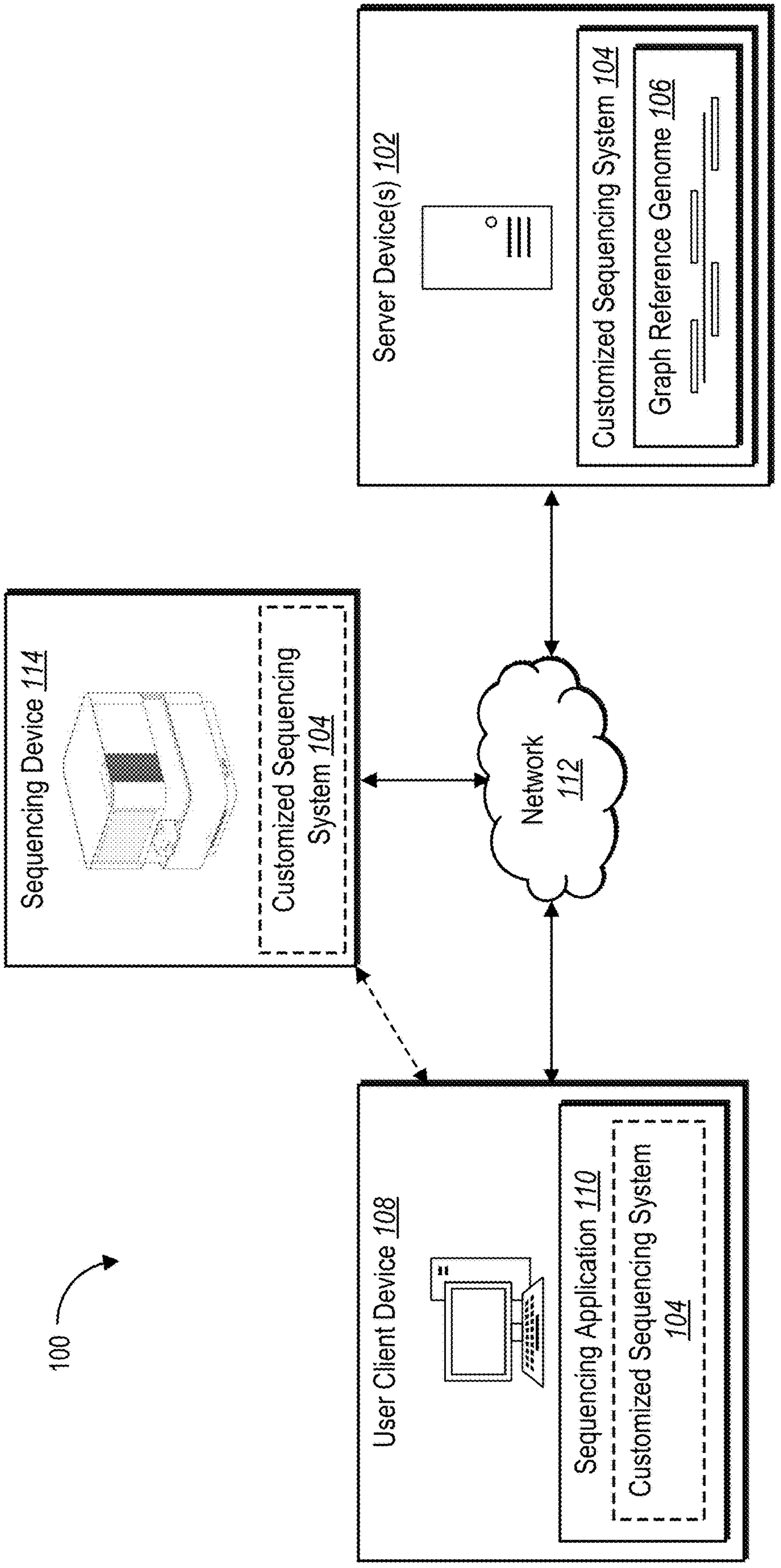
FIG. 1 illustrates a diagram of an environment in which a customized sequencing system can operate in accordance with one or more embodiments.

This disclosure describes one or more embodiments of a customized sequencing system that can generate a graph reference genome with haplotype paths customized for a specific sample genome and utilize the customized graph reference genome to determine nucleotide-base calls for the sample genome. For example, the customized sequencing system can determine single nucleotide polymorphisms (SNPs) or other variant-nucleotide-base calls surrounding a target genomic region of a sample genome and then impute haplotypes corresponding to the genomic region based on the surrounding variant nucleotide-base calls. From such imputed haplotypes and a linear reference genome, the customized sequencing system can generate, for the sample genome, a graph reference genome that includes paths representing the imputed haplotypes. Based on comparing nucleotide-fragment reads of the sample genome with paths representing imputed haplotypes for the target genomic region—and other such regions in the graph reference genome—the disclosed systems can determine nucleotide-base calls within the genomic region and other such regions. In some cases, the customized sequencing system also determines nucleotide-base calls by aligning nucleotide-fragment reads to a linear reference genome included in the customized graph reference genome.

Before identifying such a target genomic region, in one or more embodiments, the customized sequencing system receives data representing nucleotide-fragment reads for a sample genome that have been sequenced by a sequencing machine. Such data for the nucleotide-fragment reads include a sequence of nucleotide-base calls determined by the sequencing machine. After receiving the read data, the customized sequencing system can align the nucleotide-fragment reads with a linear reference genome. Based on the aligned nucleotide-fragment reads, the customized sequencing system can determine direct-nucleotide-base calls for genomic coordinates and regions of the sample genome with response to the linear reference genome.

As indicated above, when determining nucleotide-base calls, some difficult-to-call genomic regions can exhibit alignment-accuracy or base-calling-accuracy problems, among other sequencing challenges. In some embodiments, the customized sequencing system identifies difficult-to-call genomic regions (and sometimes non-difficult genomic regions) within the sample genome as target genomic regions. For example, the customized sequencing system identifies genomic regions of poor quality, such as low-confidence-call genomic regions where the nucleotide-base calls and/or nucleotide-fragment reads exhibit poor base-call-quality metrics, mapping-quality metrics, and/or depth metrics below corresponding thresholds. As a further example, the customized sequencing system can identify genomic regions that lack nucleotide-fragment reads covering some (or all) of the genomic regions.

Having identified target genomic regions, in one or more embodiments, the customized sequencing system determines variant-nucleotide-base calls surrounding respective target genomic regions. For instance, the customized sequencing system determines variant calls within a threshold distance of a target genomic region. To illustrate, the customized sequencing system can determine SNPs or other variants within a threshold number of base pairs from the target genomic region (e.g., 600 base pairs; 10,000 base pairs; or 50,000 base pairs). As explained further below, the customized sequencing system can determine SNPs (or other variants) that are part of one or more haplotypes corresponding to the target genomic region.

Based on the variant-nucleotide-base calls, the customized sequencing system imputes haplotypes for respective target regions. To illustrate, in one or more embodiments, the customized sequencing system statistically infers haplotypes for a target region from a haplotype database based on the variant nucleotide-base calls flanking the target genomic region. For instance, the customized sequencing system imputes haplotypes for a difficult-to-call region (e.g., low-confidence-call regions) from a corresponding haplotype reference panel in a database based on SNPs or other the variant-nucleotide-base calls. Accordingly, the customized sequencing system can compare SNPs or other variant-nucleotide-base calls to the haplotype reference panels to identify haplotypes likely to correspond to the target genomic region.

Based on the imputed haplotypes for genomic regions, in one or more embodiments, the customized sequencing system generates a graph reference genome customized for a sample genome. To illustrate, the customized sequencing system can generate the graph reference genome including both a linear reference genome and paths representing imputed haplotypes for the target genomic regions discussed above. In addition to difficult-to-call regions, the graph reference genome can also add or include paths representing imputed haplotypes for non-difficult genomic regions.

By using a customized graph reference genome, the customized sequencing system can determine final nucleotide-base calls for a target genomic region of a sample genome. To do so, in one or more embodiments, the customized sequencing system aligns nucleotide-fragment reads with the graph reference genome. For instance, the customized sequencing system can align nucleotide-fragment reads with a path of the graph reference genome- or a portion of the linear reference genome-having the highest quality mapping metrics for the corresponding nucleotide-fragment reads. In some embodiments, the customized sequencing system determines final nucleotide-base calls for genomic coordinates of the sample genome based on nucleotide-fragment reads aligned with either paths representing imputed haplotypes for target genomic regions or portions of the linear reference genome included in the graph reference genome.

As mentioned above, in addition or in the alternative to using a customized graph reference genome, the customized sequencing system can determine final nucleotide-base calls based on direct nucleotide-base calls, corresponding sequencing metrics, and imputed nucleotide-base calls. For example, the customized sequencing system can determine direct nucleotide-base calls (and corresponding sequencing metrics) based on nucleotide-fragment reads aligned with a linear or graph reference genome. Such direct nucleotide-base calls may include variant-nucleotide-base calls surrounding a genomic region. Based on the variant-nucleotide-base calls, the customized sequencing system can impute haplotypes for the genomic region and determine imputed nucleotide-base calls based on imputed haplotypes. As indicated above, in some cases, the customized sequencing system further generates a graph reference genome with paths representing the imputed haplotypes and further determines direct nucleotide-base calls for a sample genome using the graph reference genome. Based on the direct nucleotide-base calls, the corresponding sequencing metrics, and the imputed nucleotide-base calls, the disclosed systems determine final nucleotide-base calls. For instance, the customized sequencing system can utilize a weighted model or a base-call-machine-learning model to assign weights to both direct and imputed nucleotide-base calls to determine final nucleotide-base calls for the sample genome.

As just indicated above, in some embodiments, the customized sequencing system aligns nucleotide-fragment reads with a reference genome and determines direct nucleotide-base calls for a sample genome based on the aligned nucleotide-fragment reads. For instance, the customized sequencing system determines direct nucleotide-base calls based on aligning nucleotide-fragment reads with a linear reference genome or a graph reference genome. From the base calls of the aligned nucleotide-fragment reads covering genomic coordinates, in some cases, the customized sequencing system applies a probabilistic model (e.g., Bayesian probabilistic model) to determine direct nucleotide-base calls (e.g., direct variant-nucleotide-base calls) for the genomic coordinates of a sample genome.

While determining direct nucleotide-base calls, the customized sequencing system can determine and utilize a variety of sequencing metrics corresponding to the direct nucleotide-base calls. To illustrate, in one or more embodiments, the customized sequencing system determines depth metrics quantifying read depth of nucleotide-base calls at genomic coordinates of a sample genome. As another example, in some embodiments, the customized sequencing system determines mapping-quality metrics quantifying the quality of alignments of nucleotide-fragment reads with a reference genome. As yet another example, the customized sequencing system can determine call-data-quality metrics summarizing the quality or confidence of nucleotide-base calls.

In addition to direct nucleotide-base calls based on a reference genome, the customized sequencing system can determine imputed nucleotide-base calls based on imputed haplotypes corresponding to one or more genomic regions. As described above, in one or more embodiments, the customized sequencing system determines SNPs (or other variant-nucleotide-base calls) surrounding genomic regions of a sample genome and imputes haplotypes corresponding to the genomic regions based on the surrounding variant nucleotide-base calls. Based on the imputed haplotypes, in certain cases, the customized sequencing system statistically infers likely haplotypes to determine imputed nucleotide-base calls for the genomic regions.

Based on the direct nucleotide-base calls, the corresponding sequencing metrics, and the imputed nucleotide-base calls, the disclosed systems determine final nucleotide-base calls. In one or more embodiments, for instance, the customized sequencing system utilizes a weighted model to determine respective weights for the direct nucleotide-base calls and imputed nucleotide-base calls. In one or more embodiments, the customized sequencing system can determine weights based on the sequencing metrics corresponding to the direct nucleotide-base calls and other factors described below. From the weighted direct and imputed nucleotide base calls for genomic coordinates, the customized sequencing system can select or otherwise determine final nucleotide-base calls. For instance, in some cases, the customized sequencing system uses a base-call-machine-learning model to determine final nucleotide-base calls from direct and imputed nucleotide-base calls (e.g., by weighting).

As suggested above, the customized sequencing system provides several technical advantages and benefits over existing sequencing systems and methods. For example, the customized sequencing system improves the accuracy of read alignments and nucleotide base-calling accuracy by utilizing a graph reference genome customized for a sample genome. More specifically, the customized sequencing system generates a graph reference genome including paths representing imputed haplotypes for genomic regions of a sample genome. By utilizing a graph reference genome with paths for alternative contigs selected for a specific sample, the customized sequencing system can more accurately align nucleotide-fragment reads with the graph reference genome, especially for more complex or "difficult" regions (e.g., low-confidence-call regions), than generic graph reference genomes cluttered with irrelevant or too many alternative paths. Because of the improved alignment with the customized graph reference genome, the customized sequencing system can also determine more accurate nucleotide-base calls with a higher confidence that such calls match or differ from the reference base of a reference genome than existing sequencing systems.

In addition to improving alignment and base-calling accuracy, the customized sequencing system improves the computing speed and memory of sequencing systems using graph reference genomes. In contrast to generic graph reference genomes that include paths for irrelevant or excessive alleles, the customized sequencing system reduces the memory required to save a significantly smaller graph reference genome with fewer paths representing haplotypes that are imputed based on the variants of a sample genome. Rather than inefficiently using computing resources, such as processing and memory storage, on deciding between an excessive number of possible read-alignment matches with generic haplotype paths or allele paths, the customized sequencing system conserves computing processing and other resources by using a customized graph reference genome with fewer (and more relevant) paths representing imputed haplotypes for a sample's genomic regions and more efficient mapping due to fewer path matches.

In addition to improved accuracy, the customized sequencing system can generate a customized graph genome that is more flexible than conventional graph genomes. As suggested above, in one or more embodiments, the customized sequencing system imputes haplotypes based on selected variant-call data from a variant call file (e.g., VCF). To illustrate, in some cases, the customized sequencing system selectively identifies variant-nucleotide-base calls surrounding difficult-to-call regions (e.g., low-confidence-call regions), but not other genomic regions, from a VCF as a basis for imputing haplotypes to represent paths of a customized graph reference genome. Rather than using each variant-nucleotide-base call from a variant call file to generate a graph reference genome, as some existing sequencing systems do, the customized sequencing system can more selectively identify variant-call data upon which to customize a graph reference genome.

Additionally or alternatively, in one or more embodiments, the customized sequencing system improves the accuracy of determining base calls over existing sequencing systems in difficult-to-call genomic regions, no-read-coverage genomic regions, or other genomic regions-when determining final nucleotide-base calls based on direct and imputed nucleotide-base calls. By weighting and selecting between direct nucleotide-base calls and imputed nucleotide-base calls, the customized sequencing system can replace direct nucleotide-base calls exhibiting sequencing metrics below quality thresholds with imputed nucleotide-base calls that are more likely to be accurate at particular genomic coordinates or regions. As noted above, the customized sequencing system can determine such imputed nucleotide-base calls for target genomic regions based on statistically inferred haplotypes for the target genomic regions. Similarly, in some cases, the customized sequencing system can improve accuracy by determining and selecting imputed nucleotide-base calls (rather than direct nucleotide-base calls) for genomic regions that have little-to-no coverage by nucleotide-fragment reads. In addition to relying on direct and imputed nucleotide-base calls, in some cases, the customized sequencing system can improve the accuracy of final nucleotide-base calls for genomic regions by relying on additional indirect evidence, such as local variants, imputed haplotypes, and variant frequencies, that existing sequencing systems do not consider.

As suggested above, in some embodiments, the customized sequencing system improves accuracy of final nucleotide-base calls by utilizing a first-of-its-kind base-call-machine-learning model that analyzes both direct and imputed nucleotide-base calls. To illustrate, the base-call-machine-learning model can be trained to distinguish whether imputed nucleotide-base calls or direct nucleotide-base calls for genomic coordinates are more accurate based on sequencing metrics for training sample genomes and corresponding ground-truth base calls. More specifically, in one or more embodiments, the customized sequencing system trains the base-call-machine-learning model to determine final nucleotide-base calls based on direct nucleotide-base calls, sequencing metrics, and imputed nucleotide-base calls. Thus, the customized sequencing system can utilize the base-call-machine-learning model to efficiently and accurately determine final nucleotide-base calls based on a variety of data, including the variety of data types discussed above.

As illustrated by the foregoing discussion, the present disclosure utilizes a variety of terms to describe features and advantages of the customized sequencing system. Additional detail is now provided regarding the meaning of such terms. For example, as used herein, the term "nucleotide-fragment read" or simply "read" refers to an inferred sequence of one or more nucleotide bases (or nucleotide-base pairs) from all or part of a sample nucleotide sequence. In particular, a nucleotide-fragment read includes a determined or predicted sequence of nucleotide-base calls for a nucleotide fragment (or group of monoclonal nucleotide fragments) from a sequencing library corresponding to a genome sample. For example, in some cases, a sequencing device determines a nucleotide-fragment read by generating nucleotide-base calls for nucleotide bases passed through a nanopore of a nucleotide-sample slide, determined via fluorescent tagging, or determined from a well in a flow cell.

Additionally, as used herein, the term "nucleotide-base call" (or sometimes simply "base call") refers to a determination or prediction of a particular nucleotide base (or nucleotide-base pair) for a genomic coordinate of a sample genome or for an oligonucleotide during a sequencing cycle. In particular, a nucleotide-base call can indicate (i) a determination or prediction of the type of nucleotide base that has been incorporated within an oligonucleotide on a nucleotide-sample slide (e.g., read-based nucleotide-base calls) or (ii) a determination or prediction of the type of nucleotide base that is present at a genomic coordinate or region within a sample genome, including a variant call or a non-variant call in a digital output file. In some cases, for a nucleotide-fragment read, a nucleotide-base call includes a determination or a prediction of a nucleotide base based on intensity values resulting from fluorescent-tagged nucleotides added to an oligonucleotide of a nucleotide-sample slide (e.g., in a well of a flow cell). Alternatively, a nucleotide-base call includes a determination or a prediction of a nucleotide base from chromatogram peaks or electrical current changes resulting from nucleotides passing through a nanopore of a nucleotide-sample slide. By contrast, a nucleotide-base call can also include a final prediction of a nucleotide base at a genomic coordinate of a sample genome for a variant call file or other base-call-output file-based on nucleotide-fragment reads corresponding to the genomic coordinate or imputed haplotypes. Accordingly, a nucleotide-base call can include a base call corresponding to a genomic coordinate and a reference genome, such as an indication of a variant or a non-variant at a particular location corresponding to the reference genome. Indeed, a nucleotide-base call can refer to a variant call, including but not limited to, a single nucleotide polymorphism (SNP), an insertion or a deletion (indel), or base call that is part of a structural variant. As suggested above, a single nucleotide-base call can comprise an adenine call, a cytosine call, a guanine call, or a thymine call for DNA (abbreviated as A, C, G, T) or a uracil call (instead of a thymine call) for RNA (abbreviated as U).

As used herein, the term "direct evidence" refers to a base-call data determined from nucleotide-fragment reads aligned with a reference genome. For instance, direct evidence includes nucleotide-base calls for nucleotide-fragment reads, corresponding sequencing metrics, or other base-call data determined based on the nucleotide-fragment reads aligned with a reference genome at a target genomic coordinate or region corresponding to a nucleotide-base call. By contrast, the term "indirect evidence" represents base-call data or genomic data concerning a surrounding or neighboring genomic region of a target genomic coordinate or region. Such indirect evidence includes, but is not limited to, variant-nucleotide-base calls surrounding a target genomic coordinate or genomic region and imputed haplotypes, variant allele frequencies, and/or population haplotypes corresponding to the genomic coordinate or region. Indirect evidence does not include base-call data from nucleotide-fragment reads compared directly to a reference genome at a target genomic coordinate or region.

Relatedly, as used herein, the term "variant-nucleotide-base call" refers to a nucleotide-base call that differs or varies from a reference base (or reference bases) of a reference genome. To illustrate, a variant-nucleotide-base call can include (or be part of) an SNP, an indel, or a structural variant that differ from one or more reference bases of a reference genome. Additionally, as used herein, the term "direct nucleotide-base call" refers to a nucleotide-base call determined based on a comparison of nucleotide-fragment reads and a reference genome (e.g., a linear reference genome or graph reference genome). Accordingly, a direct nucleotide-base call includes a determination or prediction of the type of nucleotide base that is present at a genomic coordinate or region within a sample genome based on nucleotide-fragment reads covering the genomic coordinate and corresponding sequencing metrics. Further, as used herein, the term "direct invariant-nucleotide-base call" refers to a nucleotide-base call that matches a reference base from a reference genome based on a comparison of nucleotide-fragment reads and the reference genome. To illustrate, the customized sequencing system can determine a direct invariant-nucleotide-base call based on nucleotide-fragment reads aligned directly with a reference genome at the genomic coordinate corresponding to the nucleotide-base call.

As used herein, the term "impute" refers to statistically inferring or estimating a genotype for a genomic coordinate or a genomic region. More specifically, imputing can refer to statistically inferring haplotypes corresponding to a genomic region of a sample genome. For example, imputing can refer to utilizing variant-nucleotide-base calls surrounding a genomic region to determine haplotypes corresponding to that genomic region. In one or more embodiments, the customized sequencing system also utilizes reference panels from a haplotype database and a Hidden Markov model to impute haplotypes. As described further herein, the customized sequencing system can impute haplotypes for a target genomic region based on SNPs (or other variants) that not only surround or flank the target genomic region but are part of one or more haplotypes corresponding to the target genomic region. For instance, if twenty SNPs form haplotypes in a target genomic region, then the customized sequencing system can use fifteen of such SNPs determined for the target genomic region to identify which haplotypes exist in a sample genome and, thereby, impute the remaining five SNPs of one or more haplotypes for the target genomic region.

Further, as used herein, the term "imputed nucleotide-base call" refers to a nucleotide-base call for a genomic coordinate determined based on imputed haplotypes and/or variant frequencies. For instance, an imputed nucleotide-base call includes a determination or prediction of the type of nucleotide base that is present at a genomic coordinate or region within a sample genome based on variant-nucleotide-base calls surrounding or flanking the genomic coordinate or region and statistical inference. In some cases, the imputed nucleotide-base call represents a nucleotide base for a genomic coordinate or genomic region from a most probable or likely haplotype determined by imputation. To further illustrate, in some embodiments, an imputed nucleotide-base call includes an inferred or predicted nucleotide base for a genomic coordinate or region of a sample genome that reflects a variant frequency, local variant nucleotide-base calls, and/or population haplotypes corresponding to the genomic coordinate or region.

Further, as used herein, the term "final nucleotide-base call" refers to a nucleotide-base call determined for a genomic coordinate and included or used for a base-call-output file (e.g., a variant call file). To illustrate, in one or more embodiments, the term final nucleotide-base call includes (i) a nucleotide-base call included in a base-call-output file for a genomic coordinate, such as a variant-nucleotide-base call in a variant call file, or (ii) a nucleotide-base call for a genomic coordinate that is the same as a reference base and upon which the nucleotide-base call is included or excluded from the base-call-output file, such as a final determination to exclude a nucleotide-base call from a variant call file because the nucleotide-base call is the same as a reference base. As described below, the customized sequencing system can select a final nucleotide-base call from among (or based on) a direct nucleotide-base call and an imputed nucleotide-base call corresponding to the same genomic coordinate.

Also, as used herein, the term "sample genome" refers to a target genome or portion of a genome undergoing sequencing. For example, a sample genome includes a sequence of nucleotides isolated or extracted from a sample organism (or a copy of such an isolated or extracted sequence). In particular, a sample genome includes a full genome that is isolated or extracted (in whole or in part) from a sample organism and composed of nitrogenous heterocyclic bases. A sample genome can include a segment of deoxyribonucleic acid (DNA), ribonucleic acid (RNA), or other polymeric forms of nucleic acids or chimeric or hybrid forms of nucleic acids noted below. In some cases, the sample genome is found in a sample prepared or isolated by a kit and received by a sequencing device.

As also used herein, the term "haplotype" refers to nucleotide sequences that are present in an organism (or present in organisms from a population) and inherited from one or more ancestors. In particular, a haplotype can include alleles or other nucleotide sequences present in organisms of a population and inherited together by such organisms respectively from a single parent. In one or more embodiments, haplotypes include a set of SNPs on the same chromosome that tend to be inherited together. In some cases, data representing a haplotype or a set of different haplotypes are stored or otherwise accessible on a haplotype database. Additionally, an "imputed haplotype" refers to a haplotype that is estimated or statistically inferred to be present in a sample genome. For instance, an imputed haplotype can be a statistically inferred haplotype for a genomic coordinate or region based on SNPs surrounding or flanking the genomic coordinate or region. As indicated above, an imputed haplotype can include SNPs or other variant-nucleotide-base calls that surround a target genomic region and that upon which the customized sequencing system imputes the haplotype. Relatedly, a “population haplotype” refers to a haplotype present within a particular or defined population.

Additionally, as used herein, the term “genomic coordinate” refers to a particular location or position of a nucleotide base within a genome (e.g., an organism’s genome or a reference genome). In some cases, a genomic coordinate includes an identifier for a particular chromosome of a genome and an identifier for a position of a nucleotide base within the particular chromosome. For instance, a genomic coordinate or coordinates may include a number, name, or other identifier for a chromosome (e.g., chr1 or chrX) and a particular position or positions, such as numbered positions following the identifier for a chromosome (e.g., chr1: 1234570 or chr1: 1234570-1234870). Further, in certain implementations, a genomic coordinate refers to a source of a reference genome (e.g., mt for a mitochondrial DNA reference genome or SARS-COV-2 for a reference genome for the SARS-COV-2 virus) and a position of a nucleotide-base within the source for the reference genome (e.g., mt: 16568 or SARS-COV-2:29001). By contrast, in certain cases, a genomic coordinate refers to a position of a nucleotide-base within a reference genome without reference to a chromosome or source (e.g., 29727).

Further, as used herein, a “genomic region” refers to a range of genomic coordinates. Like genomic coordinates, in certain embodiments, a genomic region may be identified by an identifier for a chromosome and a particular position or positions, such as numbered positions following the identifier for a chromosome (e.g., chr1: 1234570-1234870).

As noted above, a genomic coordinate includes a position within a reference genome. Such a position may be within a particular reference genome. As used herein, the term “reference genome” refers to a digital nucleic-acid sequence assembled as a representative example (or representative examples) of genes for an organism. Regardless of the sequence length, in some cases, a reference genome represents an example set of genes or a set of nucleic-acid sequences in a digital nucleic-acid sequenced determined by scientists or statistical models as representative of an organism of a particular species. For example, a linear human reference genome may be GRCh38 or other versions of reference genomes from the Genome Reference Consortium.

Additionally, as used herein, the term “graph reference genome” may include a reference genome that includes both a linear reference genome and paths representing haplotypes or other alternative nucleic-acid sequences. In particular, a graph reference genome can include a linear reference genome and paths corresponding to imputed haplotypes identified for a particular sample genome from a haplotype database. As but one example, a graph reference genome may include the Illumina DRAGEN Graph Reference Genome hg19. By contrast, this disclosure also describes a graph reference genome that comprises a linear reference genome and paths representing imputed haplotypes selected or customized for a sample genome.

Further, as used herein, the term “low-confidence-call region” refers to a range of genomic coordinates corresponding to one or more sequencing metrics that do not satisfy one or more thresholds for the corresponding sequencing metrics. In particular, a low-confidence-call region can include a range of genomic coordinates with corresponding quality metrics or other sequencing metrics that do not satisfy thresholds for quality or alignment. To illustrate, a low-confidence-call region can include a genomic region including (in whole or in part) a VNTR, a large insertion or deletion, a region with a variety of different variations, and/or other types of genomic variations.

Also, as used herein, the term “sequencing metric” refers to a quantitative measurement or score indicating a degree to which an individual nucleotide-base call (or a sequence of nucleotide-base calls) aligns, compares, or quantifies with respect to a genomic coordinate or genomic region of a reference genome or with respect to nucleotide-base calls from nucleotide-fragment reads. For instance, a sequencing metric includes a quantitative measurement or score indicating a degree to which (i) individual nucleotide-base calls align, map, or cover a genomic coordinate or reference base of a reference genome or (ii) nucleotide-base calls compare to reference or alternative nucleotide reads in terms of mapping, mismatch, base-call quality, or other raw sequencing metrics. As explained below, sequencing metrics can include different types of quality metrics.

As just indicated, the term “quality metric” refers to a metric or other quantitative measurement indicating the accuracy, confidence, or quantity of nucleotide-base calls or nucleotide-fragment reads corresponding to one or more genomic coordinates. In particular, a quality metric comprises a value indicating the likelihood that one or more predicted nucleotide-base calls are inaccurate or nucleotide-fragment reads are misaligned or below a quantitative threshold (e.g., depth). For example, in certain implementations, a quality metric can comprise a call-data-quality metric, a read-data-quality metric, or a mapping-quality metric, as explained further below.

Further, as used herein, the term “read-data-quality metric” refers to a metric or other measurement quantifying a quality and/or certainty corresponding to a nucleotide-fragment read. In particular, a read-data-quality metric can include a metric reflecting a total number of nucleotide-bases that do not match a nucleotide-base of an example nucleic-acid sequence (e.g., a reference genome or imputed haplotype) at a particular genomic coordinate across multiple reads (e.g., all reads overlapping the particular genomic coordinate) or across multiple cycles (e.g., all cycles). Additionally, or in the alternative, a read-data-quality metric can include a metric reflecting a read-position metrics for sample nucleic-acid sequences by, for example, determining a mean or median position within a sequencing read of nucleotide-bases covering a genomic coordinate.

Additionally, as used herein, the term “call-data-quality metric” refers to a metric or other measurement quantifying an accuracy or certainty of a nucleotide-base call. A call-data-quality metric can include, for instance, base-call-quality metrics, callability metrics, or somatic-quality metrics. As for the initial example, a “base-call-quality metric” refers to a specific score or other measurement indicating an accuracy of a nucleotide-base call. In particular, a base-call-quality metric comprises a value indicating a likelihood that one or more predicted nucleotide-base calls for a genomic coordinate contain errors. For example, in certain implementations, a base-call-quality metric can comprise a Q score (e.g., a Phred quality score) predicting the error probability of any given nucleotide-base call. To illustrate, a quality score (or Q score) may indicate that a probability of an incorrect nucleotide-base call at a genomic coordinate is equal to 1 in 100 for a Q20 score, 1 in 1,000 for a Q30 score, 1 in 10,000 for a Q40 score, etc.

Further, as used herein, the term "callability metric" refers to a metric or other measurement quantifying indicating a correct nucleotide-base call (e.g., variant-nucleotide-base call) at a genomic coordinate. To illustrate, a callability metric can include a fraction or percentage of non-N reference positions with a passing genotype call, as implemented by Illumina, Inc. Further, in some implementations, the customized sequencing system 104 uses a version of Genome Analysis Toolkit (GATK) to determine callability metrics.

Additionally, as used herein, the term "somatic-quality metric" refers to a metric or other measurement estimating a probability of determining a number of anomalous nucleotide-fragment reads in a tumor sample genome. For example, a somatic-quality metric can represent an estimate of a probability of determining a given (or more extreme) number of anomalous reads in a tumor sample genome using a Fisher Exact Test-given counts of anomalous and normal reads in tumor and normal BAM files. In some cases, the customized sequencing system 104 using a Phred algorithm to determine a somatic-quality metric and expresses the somatic-quality metric as a Phred-scaled score, such as a quality score (or Q score), that ranges from 0 to 60. Such a quality score may be equal to −10 log 10 (Probability variant is somatic).

Also, as used herein, the term "mapping-quality metric" refers to a metric or other measurement quantifying a quality or certainty of an alignment of nucleotide-fragment reads or other sample nucleotide sequences with a reference genome. In particular, the term mapping-quality metric can include mapping quality (MAPQ) scores for nucleotide-base calls at genomic coordinates, where a MAPQ score represents −10 log 10 Pr {mapping position is wrong}, rounded to the nearest integer. In the alternative to a mean or median mapping quality, in some embodiments, a mapping-quality metric refers to a full distribution of mapping qualities for all nucleotide-fragment reads aligning with a reference genome at a genomic coordinate.

As further used herein, the term "depth metric" refers to a metric that quantifies the number of nucleotide-fragment reads (or number of nucleotide-base calls from nucleotide-fragment reads) that correspond or overlap a genomic coordinate of a sample genome or other nucleic-acid sequence. A depth metric can, for instance, quantify a number of nucleotide-base calls that have been determined and aligned at a genomic coordinate during sequencing. In some cases, the customized sequencing system uses a scale in which a normalized depth of 1 refers to diploid and a normalized depth of 0.5 refers to haploid. In addition, or in the alternative, the customized sequencing system can utilize a depth metric that quantifies a number of nucleotide-base calls below an expected or threshold depth coverage at a genomic coordinate or genomic region.

Further, as used herein, the term "genotype variability" refers to a degree of variation in a genotype for nucleotide bases for a particular genomic region. In particular, genotype variability can include a metric or measurement quantifying a likelihood that a genomic region and/or a haplotype will align with a graph reference genome. Additionally, in one or more embodiments, genotype variability can reflect a number or breadth of likely nucleotide bases (or nucleotide-base sequences) in a particular genomic region with respect to a reference genome.

The following paragraphs describe the customized sequencing system with respect to illustrative figures that portray example embodiments and implementations. For example, FIG. 1 illustrates a schematic diagram of a system environment (or "environment") 100 in which a customized sequencing system 104 operates in accordance with one or more embodiments. As illustrated, the environment 100 includes one or more server device(s) 102 connected to a user client device 108 and a sequencing device 114 via a network 112. While FIG. 1 shows an embodiment of the customized sequencing system 104, this disclosure describes alternative embodiments and configurations below.

As shown in FIG. 1, the server device(s) 102, the user client device 108, and the sequencing device 114 are connected via the network 112. Accordingly, each of the components of the environment 100 can communicate via the network 112. The network 112 comprises any suitable network over which computing devices can communicate. Example networks are discussed in additional detail below with respect to FIG. 11.

As indicated by FIG. 1, the sequencing device 114 comprises a device for sequencing a sample genome or other nucleic-acid polymer. In some embodiments, the sequencing device 114 analyzes nucleic-acid segments or oligonucleotides extracted from samples to generate data utilizing computer implemented methods and systems (described herein) either directly or indirectly on the sequencing device 114. More particularly, the sequencing device 114 receives and analyzes, within nucleotide-sample slides (e.g., flow cells), nucleic-acid sequences extracted from samples. In one or more embodiments, the sequencing device 114 utilizes SBS to sequence a sample genome or other nucleic-acid polymers. In addition, or in the alternative to communicating across the network 112, in some embodiments, the sequencing device 114 bypasses the network 112 and communicates directly with the user client device 108. Additionally, as shown in FIG. 1, in one or more embodiments, the sequencing device 114 includes the customized sequencing system 104.

As further indicated by FIG. 1, the server device(s) 102 may generate, receive, analyze, store, and transmit digital data, such as data for nucleotide-base calls or sequencing nucleic-acid polymers. As shown in FIG. 1, the sequencing device 114 may send (and the server device(s) 102 may receive) various data from the sequencing device 114, including data representing nucleotide-fragment reads. The server device(s) 102 may also communicate with the user client device 108. In particular, the server device(s) 102 can send data for nucleotide-fragment reads, direct nucleotide-base calls, imputed nucleotide-base calls, and/or sequencing metrics to the user client device 108. Additionally, as shown in FIG. 1, the server device(s) 102 can include the customized sequencing system 104. In one or more embodiments, as explained further below, the customized sequencing system 104 generates a graph reference genome 106 customized for a sample genome. Accordingly, the server device(s) 102 can also send the graph reference genome 106 to the user client device 108.

In some embodiments, the server device(s) 102 comprise a distributed collection of servers where the server device(s) 102 include a number of server devices distributed across the network 112 and located in the same or different physical locations. Further, the server device(s) 102 can comprise a content server, an application server, a communication server, a web-hosting server, or another type of server.

As further illustrated and indicated in FIG. 1, the user client device 108 can generate, store, receive, and send digital data. In particular, the user client device 108 can receive data for the nucleotide-fragment reads, direct nucleotide-base calls, imputed nucleotide-base calls, sequencing metrics, and/or graph reference genomes from the server device(s) 102 and/or the sequencing device 114. The user client device 108 can accordingly present final nucleotide-fragment reads within a graphical user interface to a user associated with the user client device 108.

The user client device 108 illustrated in FIG. 1 may comprise various types of client devices. For example, in some embodiments, the user client device 108 includes non-mobile devices, such as desktop computers or servers, or other types of client devices. In yet other embodiments, the user client device 108 includes mobile devices, such as laptops, tablets, mobile telephones, or smartphones. Additional details with regard to the user client device 108 are discussed below with respect to FIG. 11.

As further illustrated in FIG. 1, the user client device 108 includes a sequencing application 110. The sequencing application 110 may be a web application or a native application stored and executed on the user client device 108 (e.g., a mobile application, desktop application). The sequencing application 110 can include instructions that (when executed) cause the user client device 108 to receive data from the customized sequencing system 104 and present data from the sequencing device 114 and/or the server device(s) 102. Furthermore, the sequencing application 110 can instruct the user client device 108 to display data for nucleotide-base calls with respect to a graph reference genome, such as variant-nucleotide-base calls from a variant call file.

As further illustrated in FIG. 1, the customized sequencing system 104 may be located on the user client device 108 as part of the sequencing application 110 or on the sequencing device 114. Accordingly, in some embodiments, the customized sequencing system 104 is implemented by (e.g., located entirely or in part) on the user client device 108. As mentioned, in yet other embodiments, the customized sequencing system 104 is implemented by one or more other components of the environment 100, such as the sequencing device 114. In particular, the customized sequencing system 104 can be implemented in a variety of different ways across the server device(s) 102, the network 112, the user client device 108, and the sequencing device 114.

Though FIG. 1 illustrates the components of the environment 100 communicating via the network 112, in certain implementations, the components of environment 100 can also communicate directly with each other, bypassing the network. For instance, and as previously mentioned, in some implementations, the user client device 108 communicates directly with the sequencing device 114. Additionally, in some embodiments, the user client device 108 communicates directly with the customized sequencing system 104. Moreover, the customized sequencing system 104 can access one or more databases housed on or accessed by the server device(s) 102 or elsewhere in the environment 100.

Figure 2A:
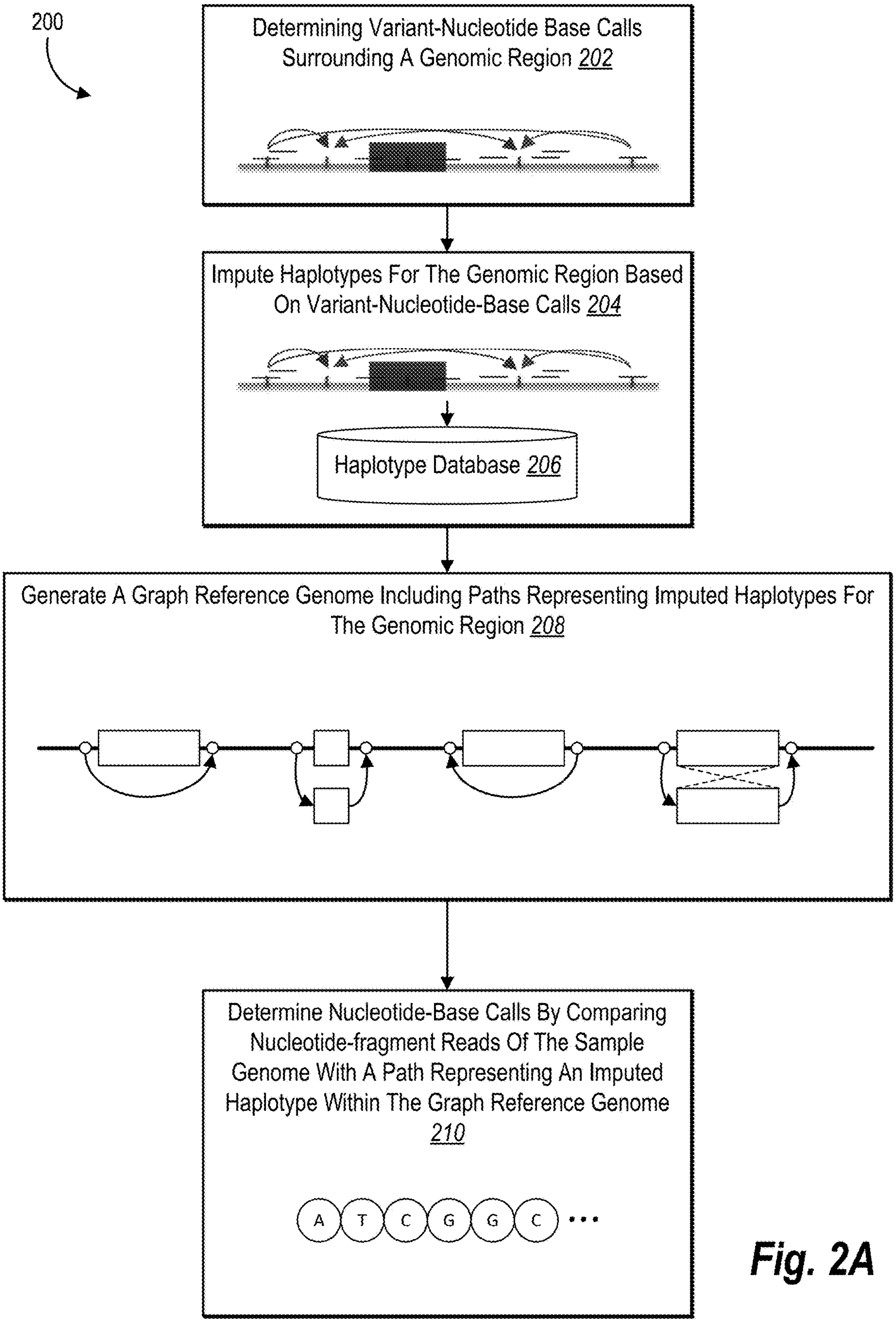
FIG. 2A illustrates an overview of the customized sequencing system generating and utilizing a graph reference genome in accordance with one or more embodiments.

As indicated above, the customized sequencing system 104 can generate a graph reference genome customized for a sample genome (or a group of sample genomes) and use the graph reference genome to determine nucleotide-base calls for the sample genome. FIG. 2A illustrates an overview of a process 200 for generating and utilizing such a customized graph reference genome. As depicted in FIG. 2A, the customized sequencing system 104 determines variant-nucleotide-base calls surrounding a particular genomic region in a sample genome. The customized sequencing system 104 subsequently utilizes the variant-nucleotide-base calls to impute haplotypes corresponding to the genomic region. The customized sequencing system 104 further generates a customized graph reference genome including paths representing the imputed haplotypes. In some embodiments, the customized sequencing system 104 then determines nucleotide-base calls for the sample genome by comparing nucleotide-fragment reads for the genomic region with paths within the graph reference genome.

As just indicated and as shown in FIG. 2A, the customized sequencing system 104 can perform an act 202 of determining variant-nucleotide-base calls surrounding a genomic region. To identify such a genomic region, in some cases, the customized sequencing system 104 sequences or receives data representing nucleotide-fragment reads for a sample genome (e.g., from one or more sequencing cycles). The customized sequencing system 104 further determines variant-nucleotide-base calls (or other nucleotide-base calls) and sequencing metrics based on a comparison of the nucleotide-fragment reads and with a reference genome (e.g., a linear reference genome). Having determined nucleotide-base calls, the customized sequencing system 104 identifies target genomic regions with nucleotide-base calls exhibiting sequencing metrics below corresponding quality thresholds.

Upon identifying a target genomic region, the customized sequencing system 104 can identify variant-nucleotide-base calls surrounding the genomic region. To illustrate, in one or more embodiments, the customized sequencing system 104 searches within a predetermined number of base pairs from the genomic region for variant-nucleotide-base calls. Specifically, in one or more embodiments, the customized sequencing system 104 identifies SNPs or other variant-nucleotide-base calls within a threshold number of base pairs within the genomic region (e.g., 10,000-50,000 base pairs from the genomic region). As noted above, such identified SNPs (or other variant-nucleotide-base calls) may be part of a haplotype that the customized sequencing system 104 imputes as present at a target genomic region. In the alternative to SNPs, in some cases, the customized sequencing system 104 identifies other variant types surrounding the genomic region, such as insertions, deletions, or inversions.

As further shown in FIG. 2A, the customized sequencing system 104 can perform an act 204 of imputing haplotypes for the genomic region based on variant-nucleotide-base calls. To illustrate, upon determining the variant-nucleotide-base calls surrounding the genomic region, the customized sequencing system 104 can impute haplotypes for the genomic region from a haplotype database 206. In one or more embodiments, the haplotype database 206 includes data representing the nucleotide-base sequences of haplotypes and other data corresponding to the haplotype, such as corresponding genomic coordinates for the haplotype, surrounding variant-nucleotide-base calls common for the haplotype, and/or populations associated with the haplotype.

In one or more embodiments, the customized sequencing system 104 imputes haplotypes for the genomic region by statistically inferring haplotypes likely to be present at the genomic region to a statistical degree of probability. More specifically, in some embodiments, the customized sequencing system 104 imputes haplotypes by comparing the variant-nucleotide-base calls surrounding the genomic region to common variant-nucleotide-base calls associated with particular haplotypes. The customized sequencing system 104 can compare SNPs surrounding the genomic region to SNPs associated with haplotypes within the haplotype database 206. To illustrate, the customized sequencing system 104 can determine SNPs that are common between the genomic region and the haplotypes in the haplotype database 206. Accordingly, in one or more embodiments, the customized sequencing system 104 utilizes statistical inference and the quantity of shared variant-nucleotide-base calls (e.g., SNPs) to identify haplotypes from the haplotype database 206 that are likely to be present at the genomic region.

In one or more embodiments, the customized sequencing system 104 utilizes the imputed haplotypes for the genomic region to generate a customized graph reference genome. To illustrate, as shown in FIG. 2A, the customized sequencing system 104 can perform an act 208 of generating a graph reference genome including paths of imputed haplotypes for the genomic region based on the variant-nucleotide-base calls. More specifically, the customized sequencing system 104 can add or generate paths representing the imputed haplotypes corresponding to a genomic region for inclusion a graph reference genome. Indeed, the customized sequencing system 104 can add such paths for multiple target genomic regions in a graph reference genome.

In one or more embodiments, the customized sequencing system 104 imputes haplotypes by identifying relevant genotypes utilizing a hidden Markov model. To illustrate, in some embodiments, the hidden Markov model identifies haplotypes by determining a likelihood that the haplotype corresponds to the genomic region. More specifically, the customized sequencing system 104 can utilize a hidden Markov model (HMM) that utilizes a haplotype database and haplotype patterns (e.g., surrounding variant-nucleotide-base calls) to identify likely haplotypes corresponding to a genomic region.

When implementing HMM imputation, for instance, the customized sequencing system 104 can utilize an imputation model based on the approach described by Na Li and Matthew Stephens, "Modeling Linkage Disequilibrium and Identifying Recombination Hotspots Using Single-Nucleotide Polymorphism Data," 165 *Genetics* 2213-2233 (2003), which is hereby incorporated by reference in its entirety. To illustrate, in some cases, the customized sequencing system 104 models the genotype of a sample genome at a target genomic region or coordinate as a mosaic of haplotypes from a reference panel. The customized sequencing system 104 further determines a probability that the sample genome includes a pair of haplotypes at the target genomic region or coordinate based on the determined variant nucleotide-base calls (e.g., SNPs) surrounding or flanking the target genomic region or coordinate. In some such cases, the customized sequencing system 104 accounts for potential linkage between (i) the target genomic region or coordinate and (ii) nearby genomic regions or coordinates by determining the probability that a haplotype is present at the target genomic region or coordinate based on the observed variant nucleotide-base calls and a similarity of the haplotypes inferred at the nearby genomic regions or coordinates. Having determined probabilities for pairs of haplotypes, in some cases, the customized sequencing system 104 selects haplotypes exhibiting a highest probability and/or above a threshold probability as the imputed haplotypes for the target genomic region or coordinate. This disclosure provides further examples and description of haplotype imputation below with reference to FIGS. 3A and 3B.

As mentioned above, the customized sequencing system 104 can utilize the customized graph reference genome to determine nucleotide-base calls for the genomic region. To illustrate, as shown in FIG. 2A, the customized sequencing system 104 performs an act 210 of determining nucleotide-base calls for the genomic region in part by comparing nucleotide-fragment reads of the sample genome with a path representing an imputed haplotype within the graph reference genome. As suggested above, the customized sequencing system 104 can likewise determine nucleotide-base calls for other genomic regions within the sample genome by comparing nucleotide-fragment reads of the sample genome with either paths representing imputed haplotypes or portions of a linear reference genome within the graph reference genome.

As just noted, in one or more embodiments, the customized sequencing system 104 aligns nucleotide-fragment reads with either the linear reference genome or paths representing imputed haplotypes to determine direct variant-nucleotide-base calls or direct invariant-nucleotide-base calls. To illustrate, the customized sequencing system 104 can align nucleotide-fragment reads with nucleotide-base calls that match a reference base from a graph reference genome. More specifically, in one or more embodiments, the customized sequencing system 104 determines a direct invariant-nucleotide-base call based on nucleotide-fragment reads aligned directly with a reference genome at the genomic coordinate or region corresponding to the nucleotide-base call. Because the customized sequencing system 104 utilizes statistical inference to determine different possible haplotype paths included in the graph reference genome, the customized sequencing system 104 can more accurately determine variant-nucleotide-base calls (or other nucleotide-base calls) for low-confidence-call regions, genomic regions with little to no coverage by nucleotide-fragment reads, or other genomic regions within a sample.

Figure 2B:
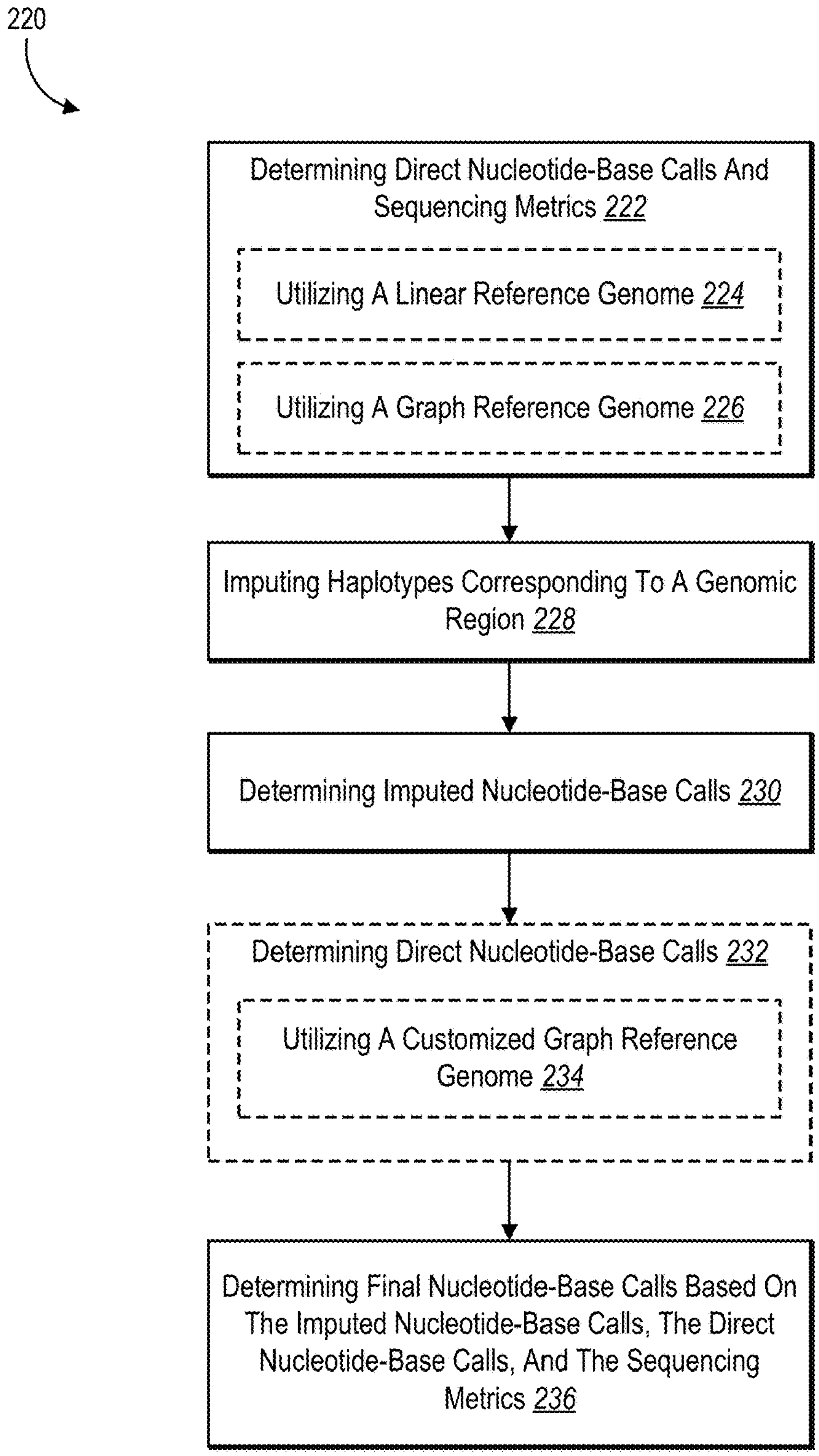
FIG. 2B illustrates an overview of the customized sequencing system determining final nucleotide-base calls based on imputed nucleotide-base calls, direct nucleotide-base calls, and sequencing metrics in accordance with one or more embodiments.

In addition to determining more accurately determining direct nucleotide-base calls based on aligned nucleotide-fragment reads, the customized sequencing system 104 can also determine and consider imputed nucleotide-base calls. To illustrate, the customized sequencing system 104 can determine nucleotide-base calls based on indirect evidence, such as variant nucleotide-base calls around or flanking a target genomic region, population haplotypes, and/or variant frequencies. FIG. 2B illustrates an overview 220 of the customized sequencing system 104 determining final nucleotide-base calls for genomic coordinates of a sample genome based on direct nucleotide-base calls with respect to a reference genome, sequencing metrics corresponding to the direct nucleotide-base calls, and imputed nucleotide-base calls for certain genomic regions of the sample genome.

As shown in FIG. 2B, for instance, the customized sequencing system 104 performs an act 222 of determining direct nucleotide-base calls and sequencing metrics. In some embodiments, the customized sequencing system 104 receives or determines nucleotide-fragment reads corresponding to a sample genome. For instance, in some cases, the customized sequencing system 104 performs SBS on the sequencing device 114 to determine nucleotide-base calls for nucleotide-fragment reads corresponding to clusters in a nucleotide-sample slide (e.g., flow cell). Alternatively, the customized sequencing system 104 receives data from a sequencing device representing nucleotide-base calls for such nucleotide-fragment reads for a sample genome.

Regardless of how the customized sequencing system 104 receives data for nucleotide-fragment reads, in one or more embodiments, the customized sequencing system 104 determines direct nucleotide-base calls for genomic coordinates or regions of a sample genome by aligning nucleotide-fragment reads to a reference genome. To illustrate, in some embodiments, the customized sequencing system 104 maps nucleotide-fragment reads for a genomic sequence to a reference genome and applies a probabilistic model (e.g., Bayesian probabilistic model) to determine direct nucleotide-base calls (e.g., variant-nucleotide-base calls) for the genomic coordinates of the sample genome. As explained further below, the customized sequencing system 104 can subsequently use the variant-nucleotide-base calls as bases for imputing haplotypes for surrounding genomic regions or as bases for determining final nucleotide-base calls.

In addition to determining direct nucleotide-base calls, the customized sequencing system 104 can also receive or determine sequencing metrics corresponding to the direct nucleotide-base calls. Such sequencing metrics can indicate various accuracy and/or certainty metrics corresponding to nucleotide-fragment reads (e.g., depth metrics, read-data-quality metrics, mapping data quality metrics). Additionally, such sequencing metrics can indicate a certainty or quality of the direct nucleotide-base calls (e.g., call-data-quality metrics, base quality dropoff (BQD) scores).

As further shown in FIG. 2B, in one or more embodiments, the act 222 includes an act 224 of utilizing a linear reference genome or an act 226 of utilizing a graph reference genome to determine direct nucleotide-base calls. As mentioned, in some embodiments, the customized sequencing system 104 receives or determines nucleotide-fragment reads corresponding to a sample genome. Accordingly, the customized sequencing system 104 can align the nucleotide-fragment reads to either a linear reference genome or a graph reference genome to determine direct nucleotide-base calls.

In addition to determining direct variant-nucleotide-base calls (or other nucleotide-base calls), in one or more embodiments, the customized sequencing system 104 determines imputed nucleotide-base calls. To illustrate, as shown in FIG. 2B, in one or more embodiments, the customized sequencing system 104 performs an act 228 of imputing haplotypes corresponding to a genomic region. As discussed above with regard to FIG. 2A, the customized sequencing system 104 can impute haplotypes corresponding to genomic coordinates of a genomic region based on variant-nucleotide-base calls surrounding or flanking the genomic region.

In one or more embodiments, the customized sequencing system 104 also utilizes other factors to impute haplotypes, including utilizing variant frequency. In some embodiments, variant frequency denotes a likelihood that a particular haplotype will occur at a target genomic coordinate or region. As further suggested above, in some embodiments, the customized sequencing system 104 imputes the most likely haplotypes for a genomic region base on "local" variant-nucleotide-base call data that denotes which genomic variants common to a particular population and/or ethnic group corresponding to a sample genome. The customized sequencing system 104 can filter or narrow down the most likely haplotypes for a genomic region based on the SNPs or other variant-nucleotide-base calls within a threshold base-pair distance of the target genomic region.

To further illustrate, in one or more embodiments, the customized sequencing system 104 utilizes population haplotype frequencies to impute haplotypes that are more likely for (or more common to) a population corresponding to the sample genome. Thus, the customized sequencing system 104 can utilize various frequency and/or population data that denotes a likelihood of a haplotype occurring to determine an imputed haplotype.

As further shown in FIG. 2B, the customized sequencing system 104 performs an act 230 of determining imputed nucleotide-base calls. In one or more embodiments, the customized sequencing system 104 determines the imputed nucleotide-base calls by identifying a nucleotide-base call for each genomic coordinate within a genomic region from a mostly likely haplotype for the genomic region. In some cases, for instance, the customized sequencing system 104 ranks the imputed haplotypes for a genomic region and selects the highest ranked imputed haplotype from which to identify the imputed nucleotide-base calls.

Additionally, as shown in FIG. 2B, the customized sequencing system 104 can optionally perform an act 232 of determining direct nucleotide-base calls, where the act 232 includes an act 234 of utilizing a customized graph reference genome. As discussed above regarding FIG. 2A, the customized sequencing system 104 can generate and utilize a customized graph reference genome. In some embodiments, the customized sequencing system 104 aligns nucleotide-fragment reads to the customized graph reference genome to determine direct nucleotide-base calls. To illustrate, the customized sequencing system 104 aligns the nucleotide-fragment reads to either a linear graph genome within the customized graph reference or the imputed haplotype paths within the customized graph reference genome to determine the direct nucleotide-base calls. In such embodiments, the customized sequencing system 104 uses the direct nucleotide-base calls determined in the act 232 with a customized graph reference genome—rather than the direct nucleotide-base calls determined in the act 222—as the basis for determining final nucleotide-base calls.

As further shown in FIG. 2B, the customized sequencing system 104 also performs an act 236 of determining final nucleotide-base calls based on the imputed nucleotide-base calls, the direct nucleotide-base calls, and the sequencing metrics. In one or more embodiments, the customized sequencing system 104 utilizes sequencing metrics to select a final nucleotide-base call for a certain genomic coordinate from either a direct nucleotide-base call or an imputed nucleotide-base call. Although imputed nucleotide-base calls may be limited to certain target genomic regions, in some cases, the customized sequencing system 104 can select a final nucleotide-base call for each genomic coordinate within a sample genome from either a direct nucleotide-base call or an imputed nucleotide-base call.

As noted above, in some embodiments, the customized sequencing system 104 utilizes a weighted model to determine final nucleotide-base calls. To illustrate, in one or more embodiments, the customized sequencing system 104 weights direct nucleotide-base calls based on sequencing metrics reflecting the quality of the direct nucleotide-base calls and/or the nucleotide-fragment reads that the nucleotide-base calls are based on. Further, in some embodiments, the customized sequencing system 104 weights imputed nucleotide-base calls based on the variability and/or frequency of the haplotypes used to determine the imputed nucleotide-base calls.

In addition or in the alternative to a weighted model, in some embodiments, the customized sequencing system 104 utilizes a machine learning model to determine the final nucleotide-base calls. As described further below, in some embodiments, the customized sequencing system 104 utilizes a base-call-machine-learning model to determine the nucleotide-base calls based on direct nucleotide-base calls, sequencing metrics, and imputed nucleotide-base calls. The customized sequencing system 104 can train the base-call-machine-learning model to predict final nucleotide-base calls by selectin either the direct nucleotide-base calls or the imputed nucleotide-base calls for genomic coordinates.

Figure 3A:
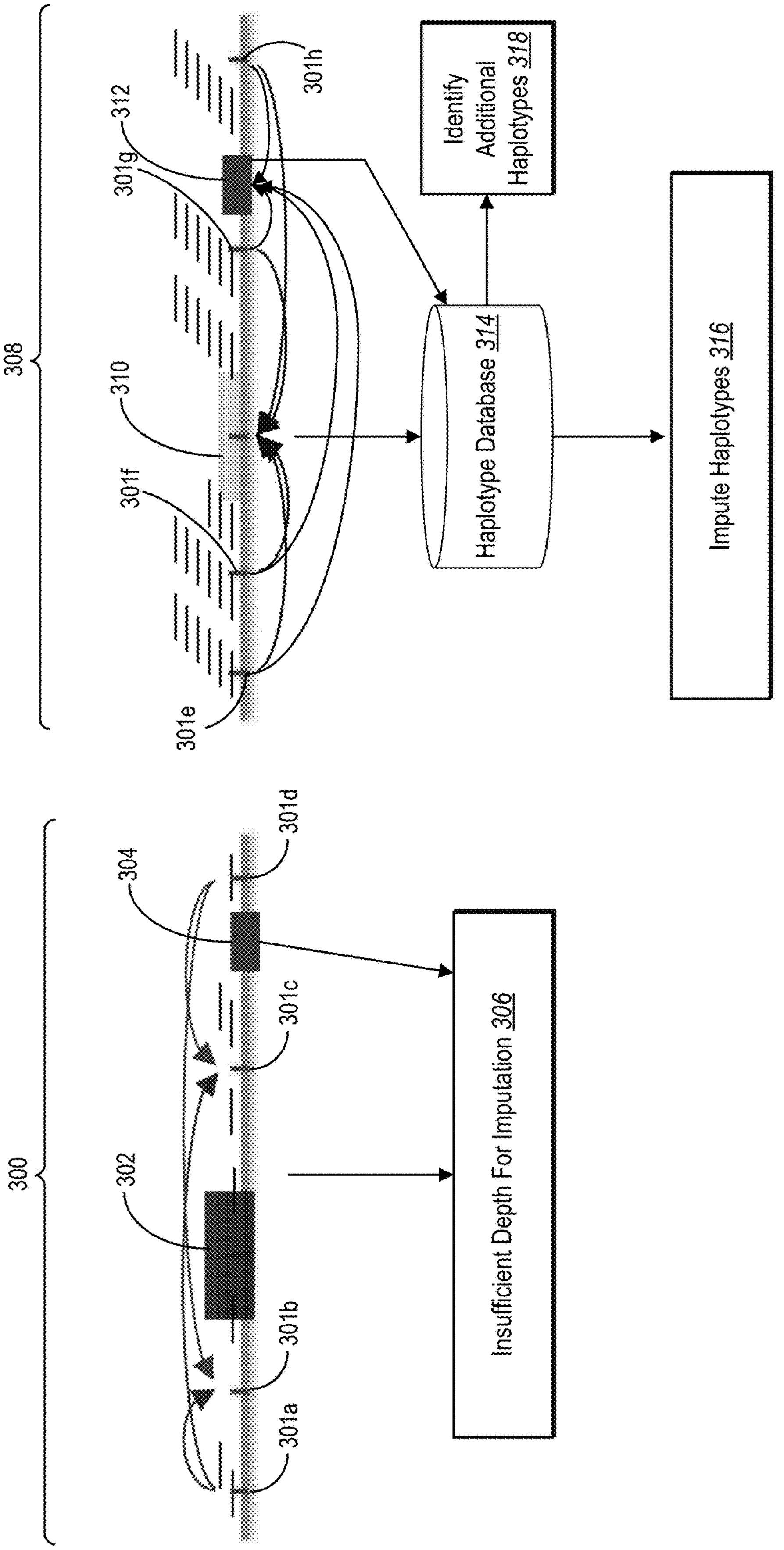
FIGS. 3A-3B illustrate an example of the customized sequencing system imputing haplotypes corresponding to a genomic region utilizing a haplotype database in accordance with one or more embodiments.
Figure 3B:
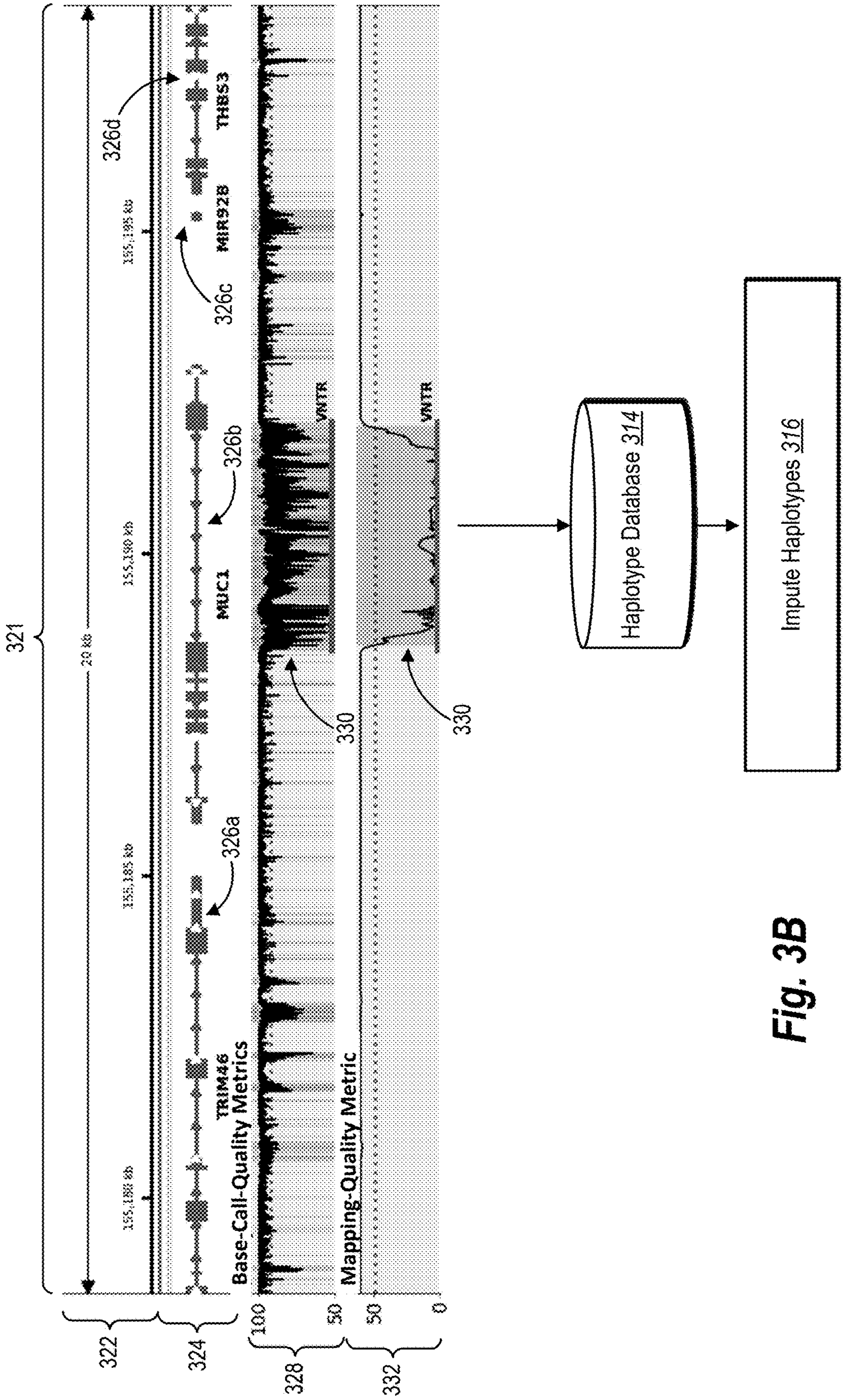

As mentioned above, in one or more embodiments, the customized sequencing system 104 imputes haplotypes for genomic regions of a sample genome. FIGS. 3A-3B illustrate the customized sequencing system 104 determining whether to impute haplotypes for genomic regions and (in some cases) imputing haplotypes for a target genomic region with respect to a linear reference genome. More specifically, FIG. 3A illustrates the customized sequencing system 104 determining not to impute haplotypes based on insufficient depth of nucleotide-fragment reads and corresponding variant nucleotide-base calls surrounding target genomic regions. By contrast, FIG. 3A also illustrates the customized sequencing system 104 determining to impute haplotypes for target regions based on variant nucleotide-base calls (derived from nucleotide-fragment reads) surrounding target genomic regions.

As suggested by FIG. 3A, the customized sequencing system 104 either utilizes a sequencing device to determine nucleotide-fragment reads for a sample genome or receives data representing the nucleotide-fragment reads for the sample genome. The customized sequencing system 104 further aligns the nucleotide-fragment reads with a linear graph reference genome. FIG. 3A accordingly illustrates a low-depth-region visualization 300 of nucleotide-fragment reads of the sample genome aligned to a linear graph reference genome. Similarly, FIG. 3A illustrates a high-depth-region visualization 308 of nucleotide-fragment reads of the same (or different) sample genome aligned to the linear graph reference genome.

As shown in FIG. 3A, the low-depth-region visualization 300 includes a low-confidence-call region 302 and a genomic region 306. By contrast, the high-depth-region visualization 308 includes a low-confidence-call region 310 and a genomic region 312. For purposes of illustration, the low-depth-region visualization 300 and the high-depth-region visualization 308 depict sample genomic regions (but not all genomic regions) for sample genomes with respect to parts of a linear reference genome.

As further suggested by FIG. 3A, the customized sequencing system 104 determines depth metrics and other sequencing metrics corresponding to nucleotide-base calls of the nucleotide-fragment reads that have been determined during sequencing and aligned at genomic coordinates of the linear reference genome. The customized sequencing system 104 can determine depth metrics utilizing a variety of scales and types. In some embodiments, for instance, the customized sequencing system 104 determines depth metrics by quantifying a number of nucleotide-fragment reads that overlap or correspond to each genomic coordinate. As suggested by FIG. 3A, for example, the customized sequencing system 104 determines (i) genomic coordinates within the low-depth-region visualization 300 have a depth of 1× to 15× per genomic coordinate and (ii) genomic coordinates within the high-depth-region visualization 308 have a depth of 30× (or more) per genomic coordinate. Further, the low-depth-region visualization 300 includes shorter nucleotide-fragment reads.

Based on the determined depth metrics, other sequencing metrics, or other factors explained below, the customized sequencing system 104 can identify low-confidence-call regions or other genomic regions from a sample genome as target genomic regions for imputation. To illustrate, in certain embodiments, the customized sequencing system 104 identifies a low-confidence-call region corresponding to nucleotide-fragment reads with mapping-quality metrics that fail to satisfy a quality threshold. For instance, the customized sequencing system 104 can identify genomic regions with nucleotide-fragment reads having MAPQ scores below a threshold MAPQ as a low-confidence-call region, such as by identifying genomic regions with MAPQ scores below a relative threshold based on a distribution of MAPQ scores.

Additionally, or alternatively, in one or more embodiments, the customized sequencing system 104 identifies low-confidence-call regions corresponding to nucleotide-base calls with call-data-quality metrics that do not satisfy a threshold call-data-quality metric. For instance, the customized sequencing system 104 can identify genomic regions with nucleotide-base calls having base-call-quality metrics below a threshold base-call-quality metric (e.g., Q20, Q30). Similarly, the customized sequencing system 104 can identify genomic regions with nucleotide-base calls having callability metrics or somatic-quality metrics respectively below a threshold callability metric or a threshold somatic-quality metric.

In addition (or in the alternative) to mapping-quality metrics or call-data-quality metrics, in some cases, the customized sequencing system 104 identifies genomic regions as low-confidence-call regions when nucleotide-fragment reads covering or overlapping a genomic region exhibit depth metrics that fail to satisfy a threshold depth metric. For instance, the customized sequencing system 104 can identify a genomic region as a low-confidence-call region when nucleotide-fragment reads covering or overlapping with the genomic region have depth metrics below an average of 20 or 30 nucleotide-fragment reads of depth.

As suggested above, the customized sequencing system 104 can also identify a genomic region as a low-confidence-call region based on a combination of quality metrics. For instance, the customized sequencing system 104 identifies a genomic region as a low-confidence-call region when a portion, percentage, or range of corresponding nucleotide-fragment reads or nucleotide-base calls fall to satisfy a threshold fraction (e.g., ⅔) of threshold quality metrics or each threshold quality metric from a set of threshold quality metrics (e.g., a threshold mapping-quality metric, a threshold call-data-quality metric, a threshold depth metric). Based on one or more of the quality metrics and corresponding threshold quality metrics described above, for instance, the customized sequencing system 104 identifies the low-confidence-call region 302 shown in the low-depth-region visualization 300 and the low-confidence-call region 310 shown in the high-depth-region visualization 308.

In addition to low-confidence-call regions, in some embodiments, the customized sequencing system 104 identifies other target genomic regions for imputation or for identifying alternative haplotypes. For instance, in some cases, the customized sequencing system 104 sometimes identifies (as target genomic regions) genomic regions for which a sequencing machine or a sequencing pipeline have historically generated sequencing metrics that do not satisfy threshold quality metrics or have historically identified alternative haplotypes above a threshold percentage (e.g., 20% or 30% of sample genomes demonstrating alternative haplotypes). As a further example, the customized sequencing system 104 sometimes identifies (as target genomic regions) genomic regions from sample genomes of a particular ethnicity or geographic region that have historically generated sequencing metrics that do not satisfy threshold quality metrics or have historically identified alternative haplotypes above a threshold percentage.

Based on one or more of the historic factors described above, for instance, the customized sequencing system 104 identifies (as target genomic regions) the genomic region 304 shown in the low-depth-region visualization 300 and the genomic region 312 shown in the high-depth-region visualization 308. To illustrate, in one or more embodiments, the customized sequencing system 104 utilizes historical sequencing data corresponding to a particular geographic region, haplotype group, ethnicity, etc. Accordingly, the customized sequencing system 104 can identify low-confidence-call regions for which a sequencing machine has generated nucleotide-base calls with sequencing metrics below a quality metric threshold, mapping quality threshold, or other corresponding quality threshold. Accordingly, in one or more embodiments, the customized sequencing system 104 includes one or more paths in the customized graph genome that represent imputed haplotypes for a historically low-confidence-call region—even if the current genome sample does not exhibit low quality in such a genomic region.

Because of the differences in depth metrics, however, the low-depth-region visualization 300 and the high-depth-region visualization 308 include genomic regions for which the customized sequencing system 104 can impute haplotypes in some cases but cannot impute haplotypes in other cases. For instance, the low-depth-region visualization 300 for the sample genome exhibits insufficient depth for nucleotide-fragment reads corresponding to variant-nucleotide-variant calls to perform haplotype imputation. In particular, the nucleotide-fragment reads corresponding to (or covering) nucleotide-variant calls 301*a*, 301*b*, and 301*c* surrounding the low-confidence-call region 302—and the nucleotide-fragment reads corresponding to (or covering) nucleotide-variant calls 301*c* and 301*d* surrounding the genomic region 304—have insufficient depth. In other words, the low-depth-region visualization 300 lacks sufficient depth (e.g., above 30×) at SNPs or other variant-nucleotide-base calls surrounding the low-confidence-call region 302 or the genomic region 304 to impute haplotypes.

By contrast, the high-depth-region visualization 308 for the sample genome exhibits sufficient depth for nucleotide-fragment reads corresponding to variant-nucleotide-variant calls to impute haplotypes for the low-confidence-call region 310. In particular, the nucleotide-fragment reads corresponding to (or covering) nucleotide-variant calls 301*e*, 301*f*, and 301*g* surrounding the low-confidence-call region 310—and the nucleotide-fragment reads corresponding to (or covering) nucleotide-variant calls 301*g* and 301*h* surrounding the genomic region 312—exhibit sufficient depth. In other words, the high-depth-region visualization 308 exhibits sufficient depth (e.g., above 30×) at SNPs or other variant-nucleotide-base calls surrounding the low-confidence-call region 310 and the genomic region 312 to impute haplotypes.

To illustrate, in one or more embodiments, the customized sequencing system 104 aligns the nucleotide-fragment reads to a linear reference genome to determine variant-nucleotide-base calls as a basis for a set of likely haplotypes from a haplotype database. Based on aligned nucleotide-fragment reads, in one or more embodiments, the customized sequencing system 104 determines SNPs from a sample genome with 30× read coverage or by utilizing the initial reads of the sequence data. As an example of using the initial reads, the first or initial fifty base pairs of a 2×150 base pair sequencing run would equate to approximately 6× read coverage for a normal 35× whole genome sequencing run. Once the first or initial fifty base pairs of such a sequencing run have been determined, in some embodiments, the customized sequencing system 104 can impute haplotypes for a target genomic region and accordingly generate a graph reference genome customized for a specific sample genome. With such coverage as outlined above, the customized sequencing system 104 can perform low-pass imputation down to approximately 1× read depth to impute haplotypes. Accordingly, in some embodiments, the customized sequencing system 104 can utilize initial reads to perform low-pass haplotype imputation.

After identifying the low-confidence-call region 310 and the genomic region 312 as target genomic regions and determining corresponding depth metrics are sufficient for imputation, the customized sequencing system 104 can utilize a haplotype database 314 to perform an act 316 of imputing haplotypes. In some embodiments, the customized sequencing system 104 utilizes the haplotype database 314 to impute haplotypes for the low-confidence-call region 310, but not the genomic region 312. By contrast, in some embodiments, the customized sequencing system 104 utilizes the haplotype database 314 to determine haplotypes for both the low-confidence-call region 310 and the genomic region 312.

In one or more embodiments, the haplotype database 314 includes a variety of haplotypes and associated data. To illustrate, the haplotype database 314 includes haplotype genomic sequences and corresponding genomic coordinates. In addition, in some embodiments, the haplotype database 314 also includes metadata corresponding to the haplotype sequences, such as surrounding variant-nucleotide-base calls common to a haplotype, populations or ethnic groups associated with the haplotype, and/or other data relating to the haplotype.

As mentioned, in one or more embodiments, the customized sequencing system 104 utilizes the haplotype database 314 to impute haplotypes. More specifically, the customized sequencing system 104 can impute haplotypes for a genomic region by identifying haplotypes from the haplotype database 314 with a sufficient likelihood of being present at the genomic region. To illustrate, the customized sequencing system 104 can compare variant-nucleotide-base calls surrounding the low-confidence-call region 310 to variant-nucleotide-base calls associated with haplotypes within the haplotype database 314. To illustrate, the customized sequencing system 104 can determine SNPs that are common between the low-confidence-call region 310 and the haplotypes in the haplotype database 314. Based on the SNPs (or other variant-nucleotide-base calls) common between the low-confidence-call region 310 and candidate haplotypes, the customized sequencing system 104 statistically infers which haplotypes are more likely present within the low-confidence-call region 310.

For example, in some embodiments, the customized sequencing system 104 applies a hidden Markov model (HMM) to impute haplotypes for the low-confidence-call region 310. To illustrate, in some embodiments, the customized sequencing system 104 can identify imputed haplotypes from the haplotype database 314 utilizing a hidden Markov model. More specifically, the customized sequencing system 104 can utilize a hidden Markov model to compare haplotype patterns (e.g., surrounding variant-nucleotide-base calls) corresponding to the genomic region and haplotypes in the haplotype database 314 to identify likely haplotypes corresponding to a genomic region. In some embodiments, for instance, the customized sequencing system 104 uses a hidden Markov model to impute haplotypes as described by Genetic Variants Predictive of Cancer Risk, WO 2013/035/114 A1 (published Mar. 14, 2013), or by A. Kong et al., Detection of Sharing by Descent, Long-Range Phasing and Haplotype Imputation, Nat. Genet. 40, 1068-75 (2008), both of which are incorporated by reference in their entirety. Additionally, or alternatively, the customized sequencing system 104 uses a hidden Markov model to impute haplotypes using available software, such as fastPHASE, BEAGLE, MACH, or IMPUTE.

In addition to imputing haplotypes, as shown in FIG. 3A, the customized sequencing system 104 performs an act 318 of identifying additional haplotypes. More specifically, in some embodiments, the customized sequencing system 104 identifies alternative haplotypes from the haplotype database 314 for the allele in the genomic region 312 at the genomic region 312. For example, in one or more embodiments, the system identifies highly common haplotypes for the genomic region 312 for inclusion in the graph reference genome. In some embodiments, the customized sequencing system 104 identifies haplotypes present above a specified threshold (e.g., 20% or 30%) for one or more ethnicities and/or geographic regions corresponding to the sample genome.

As noted above, the customized sequencing system 104 can impute haplotypes for a variety of genomic regions. For example, the customized sequencing system 104 can impute haplotypes for a genomic region including (in whole or in part) a VNTR, a structural variant, an insertion, a deletion, or an inversion. Accordingly, a target genomic region may include some or all of a set of nucleotide bases (or set of missing nucleotide bases) corresponding or representing a VNTR, a structural variant, an insertion, a deletion, or an inversion. FIG. 3B illustrates an example of a low-confidence-call region for which the customized sequencing system 104 imputes haplotypes. More specifically, FIG. 3B illustrates reference data and sequencing metrics for a portion of a sample genome 321. In particular, FIG. 3B illustrates genomic-coordinate markers 322 from a linear reference genome that correspond to the portion of the sample genome 321 and gene-encoding regions 324 from the linear reference genome that correspond to the portion of the sample genome 321. As indicated by the genomic-coordinate markers 322, the portion of the sample genome 321 is 20 kilobases long with genomic coordinates ranging from approximately kilobase 155,180 to kilobase 155,200. Within this range, the reference genome includes a gene 326*a* for TRIM46, a gene 326*b* for MUC1, a gene 326*c* for MIR92B, and a gene 326*d* for THBS3.

In addition to reference data, FIG. 3B illustrates a base-call-quality graphic 328 for base-call-quality metrics and a mapping-quality graphic 332 for mapping-quality metrics corresponding to the portion of the sample genome 321. To illustrate, the base-call-quality graphic 328 indicates a fraction or percentage of nucleotide-base calls within the portion of the sample genome 321 that satisfy a threshold metric (e.g., Q30 or Q37), where a length of the dark bars indicates a greater fraction or percentage of nucleotide-base calls with base-call-quality metrics that fail to satisfy the threshold metric. In addition to the base-call-quality graphic 328, FIG. 3B illustrates the mapping-quality graphic 332. The mapping-quality graphic 332 indicates a fraction or percentage of nucleotide-fragment reads corresponding the portion of the sample genome 321 that satisfy a threshold metric (e.g., a relative MAPQ score or MAPQ 40), where a length of the dark bars indicates a greater fraction or percentage of nucleotide-fragment reads with mapping-quality metrics that fail to satisfy the threshold metric.

As indicated above, in some embodiments, the customized sequencing system 104 can utilize the base-call-quality metrics and/or the mapping-quality metrics to identify a low-confidence-call region corresponding to one or more poor quality metrics. As shown in FIG. 3B, for instance, the customized sequencing system 104 identifies a low-confidence-call region 330 corresponding to lower quality metrics for both the base-call-quality metrics and the mapping-quality metrics. Specifically, the low-confidence-call region 330 includes (in whole or in part) a VNTR within the gene 326*b* for MUC1.

As suggested above, the customized sequencing system 104 can utilize the haplotype database 314 to perform the act 316 of imputing haplotypes for the low-confidence-call region 330. To illustrate, the customized sequencing system 104 can impute haplotypes for the low-confidence-call region 330 by determining haplotypes from the haplotype database 314 that are likely to exist at the low-confidence-call region 330. As described above, in some embodiments, the customized sequencing system 104 can determine SNPs (or other variant-nucleotide-base calls) that surround both the low-confidence-call region 330 and the haplotypes in the haplotype database 314 corresponding (or within the genomic coordinates for) the low-confidence-call region 330. Based on SNPs within a threshold number of base pairs of the low-confidence-call region 330 and that match haplotypes from the haplotype database 314, for instance, the customized sequencing system 104 imputes haplotypes for the low-confidence-call region 330.

Figure 4A:
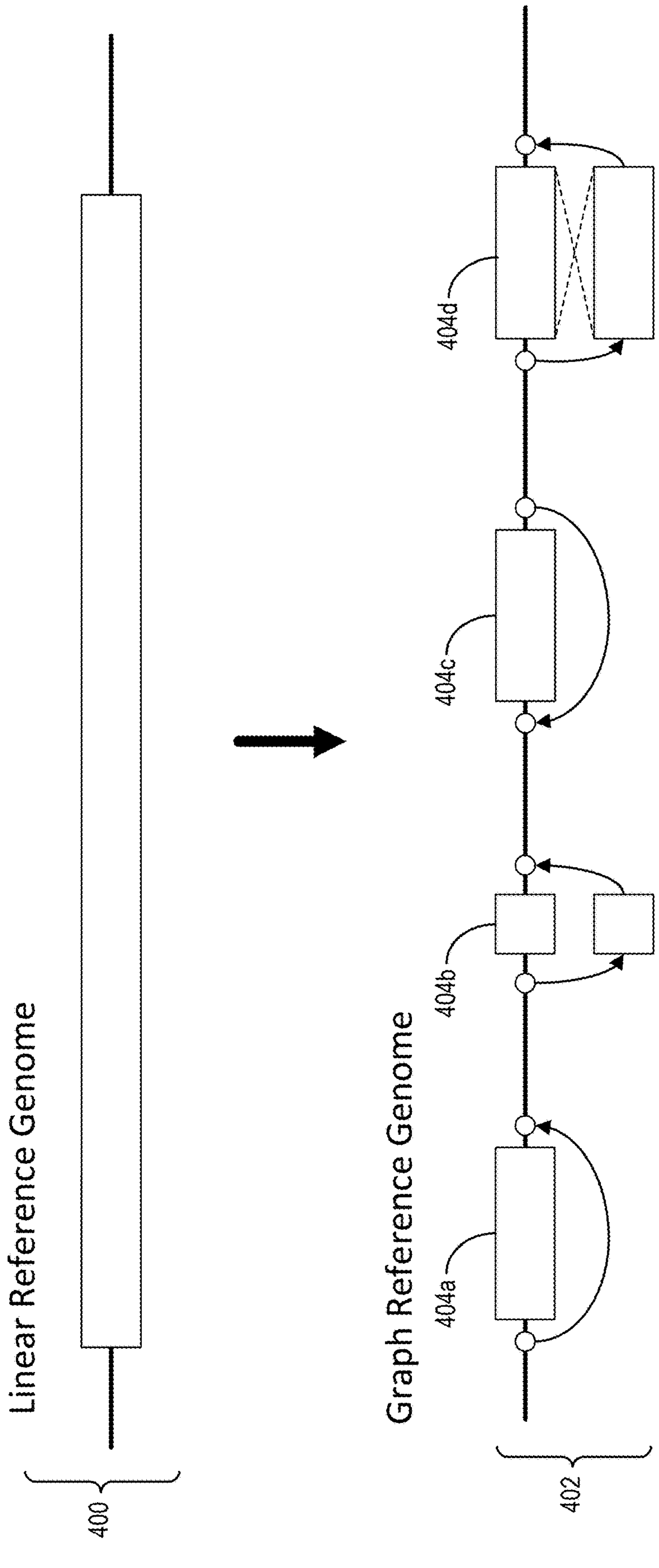
FIGS. 4A-4B illustrate the customized sequencing system generating a graph reference genome and aligning nucleotide-fragment reads of a sample genome with the graph reference genome in accordance with one or more embodiments.

As mentioned above, the customized sequencing system 104 can generate a customized graph reference genome for a particular sample genome by using imputed haplotypes for target genomic regions. FIG. 4A illustrates an overview of the customized sequencing system 104 generating such a customized graph reference genome for a particular sample genome. More specifically, FIG. 4A illustrates the customized sequencing system 104 generating a graph reference genome 402 comprising both a linear reference genome 400 and paths 404*a*-404*d* representing imputed haplotypes corresponding to various genomic regions of the sample genome.

As just noted, the graph reference genome 402 includes the linear reference genome 400. Accordingly, the customized sequencing system 104 generates the graph reference genome 402 using the linear reference genome 400 as a baseline for backwards compatibility. In other words, the customized sequencing system 104 can align nucleotide-fragment reads from the sample genome with any portion of the linear reference genome 400 prior to determining final nucleotide-base calls.

In addition to the linear reference genome 400, the graph reference genome 402 includes the paths 404*a*-404*d* representing haplotypes corresponding to the genomic region. The paths 404*a*-404*d* accordingly represent imputed haplotypes that differ from the haplotypes already present within the linear reference genome 400 for particular genomic regions. To illustrate, the path 404*a* represents a deletion with respect to the linear reference genome 400, the path 404*b* includes a single nucleotide variant differing from a reference base of the linear reference genome 400, the path 404*c* includes a duplication of (or insertion of a duplicate from) a nucleotide subsequence from the linear reference genome 400, and the path 404*d* includes an inversion of a nucleotide subsequence from the linear reference genome 400. Each of the paths 404*a*-404*d* accordingly represent an imputed haplotype for a genomic region that varies from the haplotype already present within the linear reference genome 400.

As shown in FIG. 4A, the paths 404*a*-404*d* are depicted by way of example, and the customized sequencing system 104 can determine a variety of paths from a variety of imputed haplotypes. Although not depicted in FIG. 4A, the customized sequencing system 104 can include paths representing different imputed haplotypes for a single genomic region within a graph reference genome. For example, the customized sequencing system 104 can include two or three most likely alternative haplotypes for the genomic region. To illustrate, the customized sequencing system 104 determines that a first haplotype and a second haplotype are each present in 30% of sample genomes that have the same surrounding variant-nucleotide-base calls observed in the sample genome. The customized sequencing system 104 can include paths in the graph reference genome representing the first haplotype and the second haplotype based on their respective probability in light of the variant-nucleotide-base calls.

As mentioned above, the customized sequencing system 104 can align nucleotide-fragment reads from the sample genome to the graph reference genome 402 to determine final nucleotide-base calls for the genomic region. Because the graph reference genome 402 includes both a linear reference genome and the paths 404*a*-404*d* based on imputed haplotypes, the customized sequencing system 104 can align nucleotide-fragment reads with either or both of the linear reference genome 400 and the paths 404*a*-404*d*.

Figure 4B:
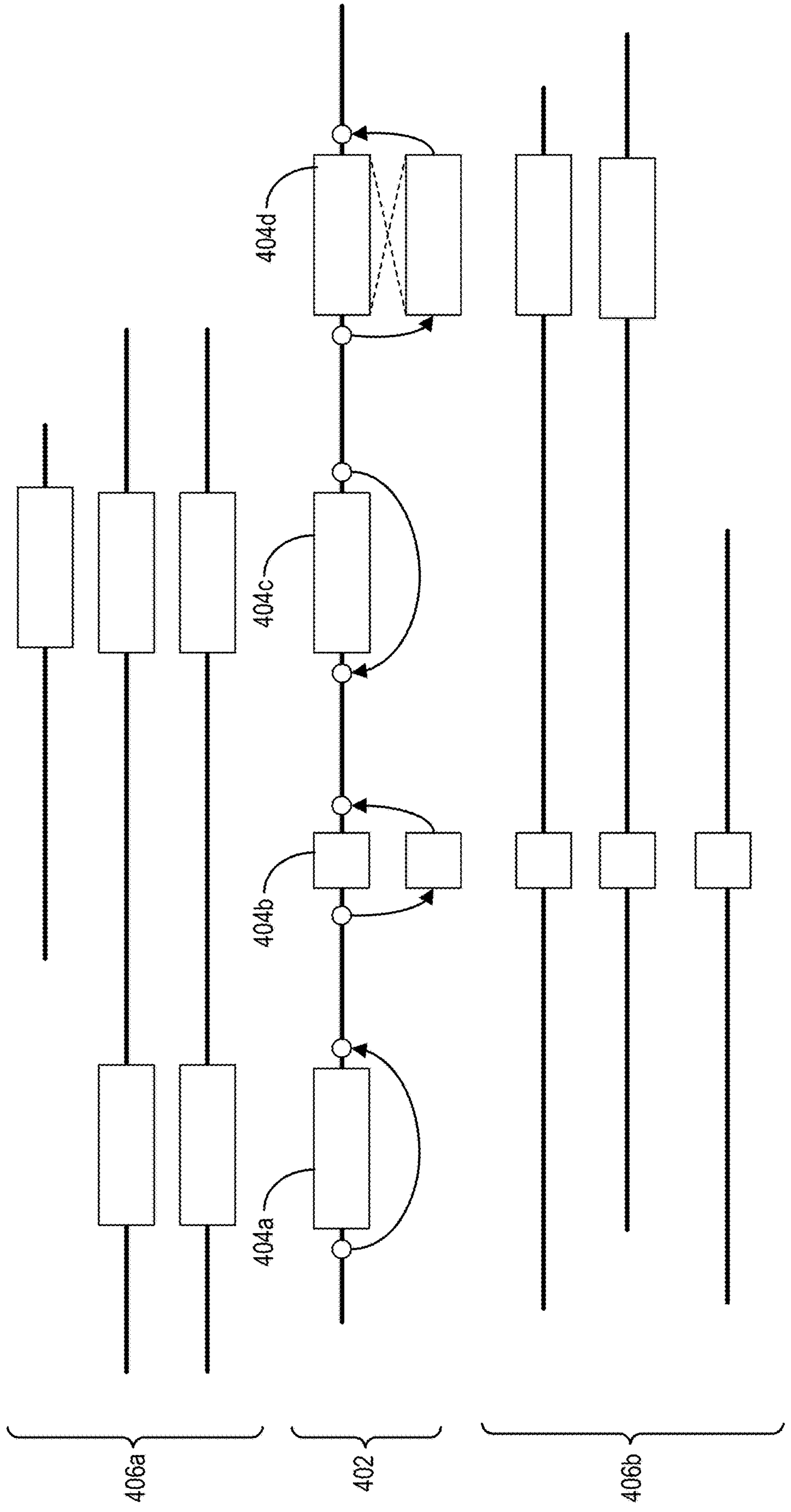

FIG. 4B illustrates the customized sequencing system 104 aligning nucleotide-fragment reads from a sample genome with the graph reference genome 402 along several genomic regions including paths representing imputed haplotypes. As shown in FIG. 4B, the customized sequencing system 104 aligns nucleotide-fragment reads 406*a* and 406*b* with the graph reference genome 402 in part by aligning variants from the nucleotide-fragment reads 406*a* and 406*b* with the paths 404*a*-404*d* corresponding to the imputed haplotypes.

As indicated by FIG. 4B, the sample genome is heterozygous at some genomic regions. As indicated by the alignment for the nucleotide-fragment reads 406*a*, the sample genome includes alleles that align with the paths 404*a* and 404*c*, but not with the path 404*b*. By contrast and as indicated by the alignment for the nucleotide-fragment reads 406*b*, the sample genome includes alleles that align with the paths 404*b* and 404*d*, but not with the paths 404*a* and 404*c*. Because the graph reference genome 402 includes both the linear reference genome 400 and the paths 404*a*-404*d*, the customized sequencing system 104 successfully aligns each read from the nucleotide-fragment reads 406*a* and 406*b* with the graph reference genome 402.

Because the sample genome includes different alleles at the genomic coordinates or regions depicted in FIG. 4Be, the customized sequencing system 104 would likely misalign or align with less accuracy one or more of the nucleotide-fragment reads 406*a* or 406*b* with the linear reference genome 400 by itself. Accordingly, the customized sequencing system 104 improves alignment by utilizing the graph reference genome 402 comprising the paths 404*a*-404*d* representing imputed haplotypes for particular genomic regions of the sample genome. Because the graph reference genome 402 includes imputed haplotypes more likely to be present in the sample genome at low-confidence-call regions (or at other genomic regions) than other excluded haplotypes, the customized sequencing system 104 increases the probability of accurate alignment over a conventional linear reference genome.

In part due to such improved alignment, the customized sequencing system 104 likewise can improve the confidence of determining variant-nucleotide-base calls (or other final nucleotide-base calls) with respect to the graph reference genome 402. Having better aligned the nucleotide-fragment reads 406*a* and 406*b* with the graph reference genome 402, the customized sequencing system 104 is more likely to accurately determine whether the sample genome includes nucleotide bases that vary or match reference bases of either the linear reference genome 400 or the imputed haplotypes represented by the paths 404*a*-404*d*.

Figure 5:
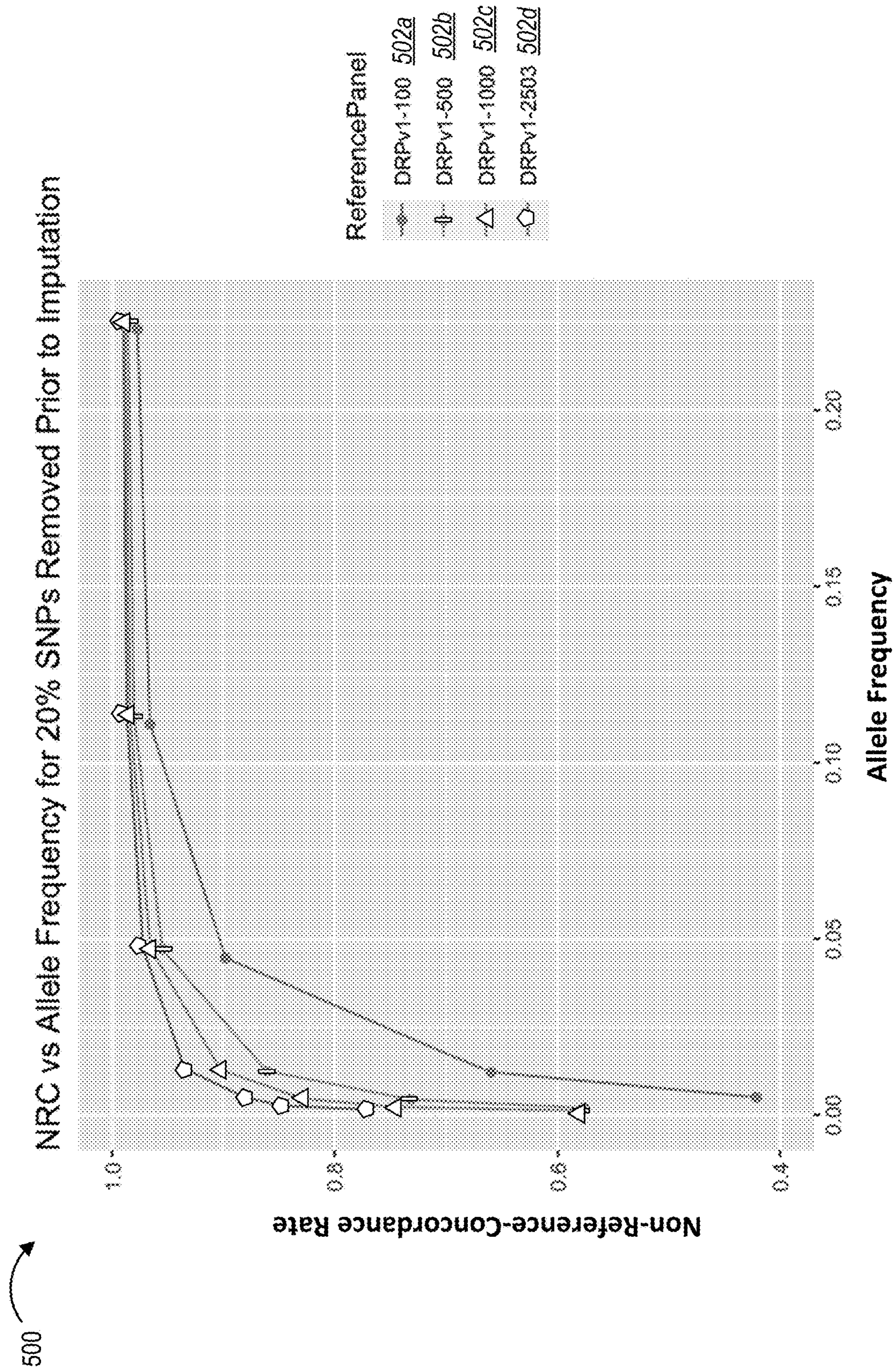
FIG. 5 illustrates a graph depicting non-reference-genotype-concordance rates for the customized sequencing system using a sample-specific graph reference genome relative to allele frequency in accordance with one or more embodiments.

As part of improving alignment and base-calling accuracy, in some embodiments, the customized sequencing system 104 uses a haplotype database comprising panels of haplotypes from different sample sizes. In accordance with one or more embodiments, FIG. 5 illustrates a graph 500 with receiver operating characteristics (ROC) curves defining an area under curve (AUC) for the non-reference-concordance rate at which a sequencing system accurately imputes SNPs of varying allele frequencies based on reference panels of different sample sizes. As indicated by FIG. 5, the ROC curves show that the customized sequencing system 104 more accurately imputes SNPs as the sample size of a reference panel in a haplotype data base increases.

To test the accuracy of imputation for different reference panels, for example, researchers removed approximately 20% of SNPs from data representing samples sequenced by a sequencing machine. The customized sequencing system 104 subsequently imputed haplotypes for the SNPs from the samples based on reference panels of varying sample size. As indicated by FIG. 5, a first reference panel 502*a* includes about 200 haplotypes from 100 samples, a second reference panel 502*b* includes about 1,000 haplotypes from 500 samples, a third reference panel 502*c* includes about 2,000 haplotypes from 1,000 samples, and a fourth reference panel 502*d* included about 5,006 haplotypes from 2,503 samples.

As shown in the graph 500, the ROC curve for the customized sequencing system 104 using the first reference panel 502*a* with 100 samples indicates a lowest non-reference-concordance rate for imputing the removed SNPs across allele frequencies for the SNPs. By contrast, the ROC curve for the customized sequencing system 104 using the fourth reference panel 502*d* with 2,503 samples indicates a highest non-reference-concordance rate for imputing the removed SNPs across allele frequencies for the SNPs. Regardless of the ROC curve, however, the non-reference-concordance rate increases with the allele frequency before plateauing at maximum concordance at an allele frequency at just above 0.10. Accordingly, in some embodiments, the customized sequencing system 104 uses a haplotype database with a reference panel of 2,503 samples or more to increase the accuracy of imputed haplotypes.

In addition to using a haplotype database with reference panels of relatively high sample size or of any sample size, as indicated above, the customized sequencing system 104 increases an accuracy of imputing haplotypes for genomic regions as depth of nucleotide-fragment reads increases for genomic coordinates with SNPs surrounding a target genomic region. For instance, in some embodiments, the customized sequencing system 104 uses SNPs based on nucleotide-fragment reads with 30× depth to impute haplotypes. Even with the same reference panel, SNPs from nucleotide-fragment reads with 30× depth give roughly three times the variant information from SBS of a whole genome than low pass whole genome sequencing (lpWGS).

Figure 6:
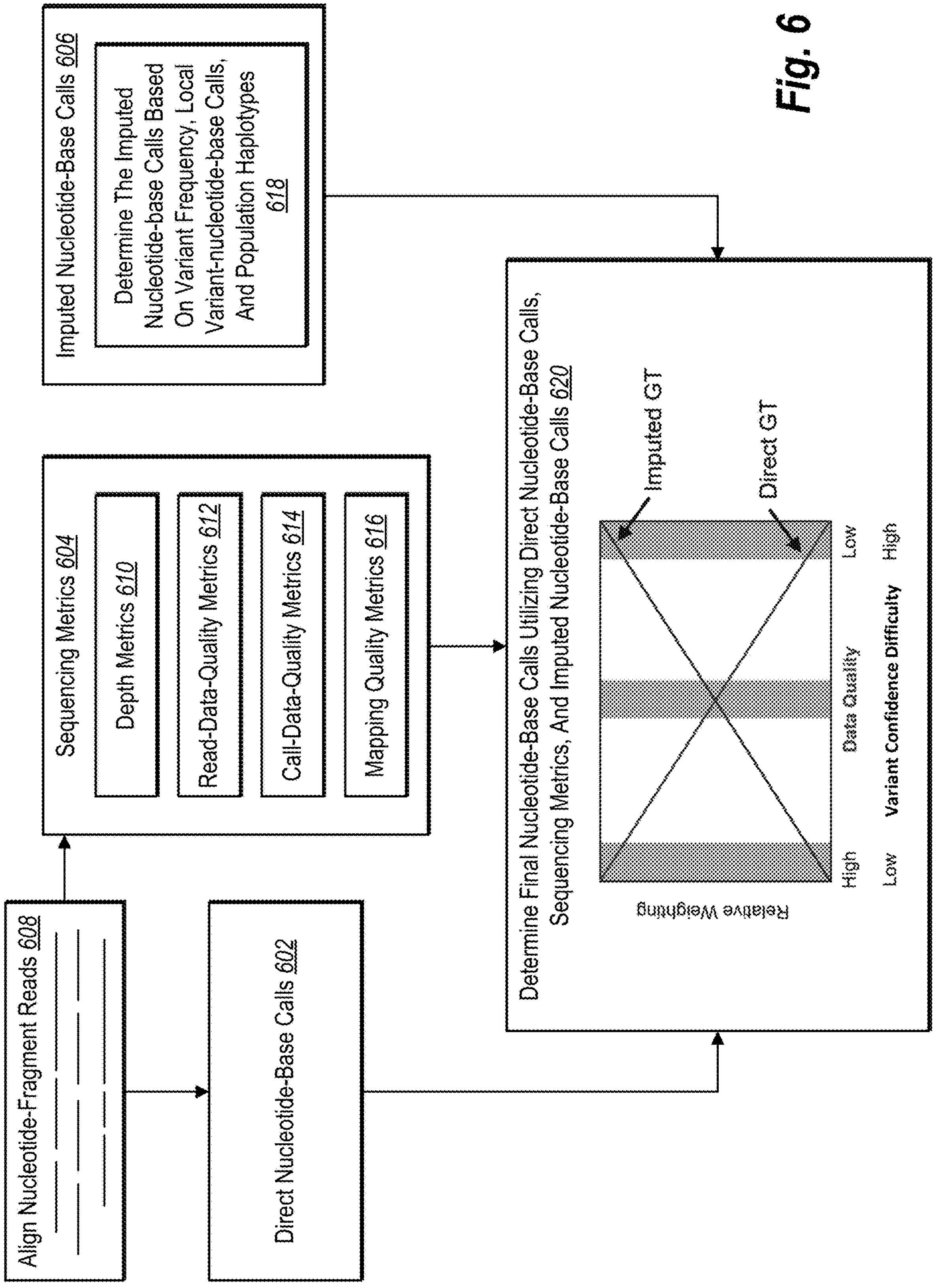
FIG. 6 illustrates the customized sequencing system utilizing direct nucleotide-base calls, sequencing metrics, and imputed nucleotide-base calls to determine final nucleotide-base calls in accordance with one or more embodiments.

As mentioned above, in one or more embodiments, the customized sequencing system 104 determines final nucleotide-base calls for a sample genome based on direct nucleotide-base calls, sequencing metrics, and indirect nucleotide-base calls. FIG. 6 illustrates an example of the customized sequencing system 104 weighting direct nucleotide-base calls and imputed nucleotide-base calls in a weighted model to determine final nucleotide-base calls with respect to a reference genome. Additionally, as will be discussed below with regard to FIGS. 7A-7B, the customized sequencing system 104 can utilize a machine learning model to determine such final nucleotide-base calls.

As shown in FIG. 6, the customized sequencing system 104 can perform an act 608 of aligning nucleotide-fragment reads with a reference genome. As discussed above with regard to FIGS. 4A-4B, the customized sequencing system 104 can align nucleotide-fragment reads sequenced from a sample genome with a either a linear reference genome or a graph reference genome.

As suggested above, the customized sequencing system 104 aligns each nucleotide-fragment read with the reference genome to determine direct nucleotide-base calls 602 with respect to a reference genome—including variant-nucleotide-base calls. To illustrate, the customized sequencing system 104 determines the direct nucleotide-base calls 602 based on nucleotide-fragment reads and alignment to either a linear reference genome or a graph reference genome. Accordingly, the customized sequencing system 104 determines the direct nucleotide-base calls 602 based on "direct" evidence from the sample genome. As suggested above, in some embodiments, this direct evidence includes aligning to paths representing haplotypes in a graph reference genome.

In addition to such direct nucleotide-base calls, the customized sequencing system 104 determines sequencing metrics 604 corresponding to the nucleotide-fragment reads and/or the direct nucleotide-base calls, including for mapping. In some cases, the sequencing metrics 604 reflect a quality and/or certainty of the nucleotide-fragment reads, nucleotide-base calls, and/or alignment thereof. To illustrate, as shown in FIG. 6, the sequencing metrics 604 can include depth metrics 610, read-data-quality metrics 612, call-data-quality metrics 614, and/or mapping-quality metrics 616.

For example, the customized sequencing system 104 can determine the depth metrics 610 as a quantification of the depth of nucleotide-base calls determined and aligned at a particular genomic coordinate during sequencing. Indeed, in some embodiments, the customized sequencing system 104 determines the depth metrics 610 for a genomic region of a sample genome based on an average of the depth of genomic coordinates within the genomic region. As mentioned above, the customized sequencing system 104 can also utilize a variety of scales and metric types for the depth metrics 610. For example, in some embodiments, the customized sequencing system 104 determines a depth metric quantifying a number of nucleotide-base calls below a threshold depth coverage.

As noted above, the customized sequencing system 104 can also determine the read-data-quality metrics 612 for nucleotide-fragment reads from a sample genome. To illustrate, in one or more embodiments, the customized sequencing system 104 determines the read-data-quality metrics 612 based on a total number of nucleotide-bases in a sample genome that do not match a nucleotide base of a reference genome, including one or more paths of a graph reference genome. Additionally, or in the alternative, the customized sequencing system 104 can determine the read-data-quality metrics 612 across multiple cycles during sequencing. Further, the customized sequencing system 104 can determine the read-data-quality metrics 612 based on read-position metrics for a sample genome by determining a mean or median position within nucleotide-fragment reads covering a genomic coordinate within the sample genome.

In some embodiments, the customized sequencing system 104 further determines the call-data-quality metrics 614 corresponding to nucleotide-base calls for either nucleotide bases within nucleotide-fragment reads or direct nucleotide-base calls with respect to a reference genome. In some embodiments, the customized sequencing system 104 determines the call-data-quality metrics 614 by quantifying a quality and/or certainty corresponding to a nucleotide-base call. For instance, the customized sequencing system 104 can determine a base-call-quality metric (e.g., a Phred quality score or Q score) predicting the error probability of any given nucleotide-base call within a sequencing cycle for a nucleotide-fragment read or any given direct nucleotide-base call for a genomic coordinate with respect to a reference genome. To illustrate, in some embodiments, the customized sequencing system 104 determines the call-data-quality metrics 614 as a percentage or subset of nucleotide-base calls within a genomic region satisfying a threshold quality score, such as Q20. Additionally or alternatively, the customized sequencing system 104 determines callability metrics or somatic-quality metrics as the call-data-quality metrics 614 for either nucleotide bases within nucleotide-fragment reads or direct nucleotide-base calls.

As further noted above, the customized sequencing system 104 can determine the mapping-quality metrics 616 for nucleotide-fragment reads from a sample genome. In some embodiments, the customized sequencing system 104 determines the mapping-quality metrics 616 by quantifying a quality and/or certainty of an alignment of nucleotide-fragment reads with a reference genome. In some embodiments, the customized sequencing system 104 determines mapping quality (MAPQ) scores for nucleotide-base calls of nucleotide-fragment reads at genomic coordinates. To illustrate, in one or more embodiments, the customized sequencing system 104 determines a MAPQ score representing −10 log 10 Pr {mapping position is wrong}, rounded to the nearest integer. In some embodiments, the customized sequencing system 104 determines a mean or median of mapping-quality metrics for nucleotide-fragment reads within a genomic region of sample region.

In addition to determining the direct nucleotide-base calls 602, the customized sequencing system 104 determines imputed nucleotide-base calls 606. To illustrate, in one or more embodiments, the customized sequencing system 104 determines the imputed nucleotide-base calls 606 based on "indirect" evidence corresponding to statistical information related to variants relative to a particular sample genome. As shown in FIG. 6, in one or more embodiments, determining the imputed nucleotide-base calls 606 can include an act 618 of determining the imputed nucleotide-base calls 606 based on local nucleotide-base calls, population haplotypes, and variant frequencies.

More specifically, in one or more embodiments, the customized sequencing system 104 determines and utilizes population data corresponding to a sample genome. To illustrate, in some embodiments, the customized sequencing system 104 identifies or receives data regarding a population and/or ethnic group corresponding to a particular sample genome. Accordingly, the customized sequencing system 104 can identify local nucleotide-base calls common for the population. To illustrate, in one or more embodiments, the customized sequencing system 104 utilizes a reference genome corresponding to the identified population or ethnic group corresponding to the sample genome. Further, in some embodiments, the customized sequencing system 104 identifies nucleotide-base calls at the genomic coordinates of the genomic region in the sample genome. Thus, the customized sequencing system 104 can utilize the identified nucleotide-base calls as a reference point for haplotypes upon which to determine the imputed nucleotide-base calls 606.

As just suggested and mentioned above, the customized sequencing system 104 determines or receives population data corresponding to a sample genome. Accordingly, the customized sequencing system 104 can determine population haplotype frequencies corresponding to the sample genome by identifying haplotypes corresponding to the population specific to the sample genome. In one or more embodiments, the customized sequencing system 104 utilizes a haplotype database to identify the population haplotypes, such as by identifying a reference panel specific to a geographic region or ethnic group.

Additionally, the customized sequencing system 104 can utilize variant frequencies to determine the imputed nucleotide-base calls 606. In one or more embodiments, the customized sequencing system 104 identifies genomic variants corresponding to the population identified for the sample genome. More specifically, the customized sequencing system 104 can identify genomic variants that correspond to the genomic coordinates of genomic regions (e.g., low-confidence-call genomic regions) identified for the sample genome. Accordingly, the customized sequencing system 104 can identify nucleotide-base calls corresponding to frequent variants for the population and at the particular genomic region. Thus, in one or more embodiments, the customized sequencing system 104 utilizes the nucleotide-base calls from the identified variants as the imputed nucleotide-base calls 606.

As described above, in some embodiments, the customized sequencing system 104 utilizes the population haplotypes to impute haplotypes for genomic coordinates or target genomic regions of a sample genome based on a reference panel or other population haplotypes. To illustrate, the customized sequencing system 104 can impute haplotypes corresponding to a genomic region based on surrounding variant-nucleotide-base calls. In addition, in some embodiments, the customized sequencing system 104 utilizes variant frequencies and population data to determine the imputed haplotypes. Further, the customized sequencing system 104 can determine an imputed nucleotide-base call based on the imputed haplotypes. More specifically, in some embodiments, the customized sequencing system 104 ranks imputed haplotypes according to likelihood for a genomic coordinate or region and determines an imputed nucleotide-base call from the highest ranked haplotype for the genomic coordinate or region.

In some embodiments, the customized sequencing system 104 determines the imputed nucleotide-base calls 606 based on one or more of the nucleotide-base calls corresponding to the local nucleotide-base calls, the nucleotide-base calls corresponding to the population haplotypes, and the nucleotide-base calls corresponding to the frequent variants. To illustrate, in one or more embodiments, the customized sequencing system 104 selects the imputed nucleotide-base calls 606 based on nucleotide-base calls having the highest likelihood based on frequencies of one or more of the local nucleotide-base calls, population haplotypes, and variant frequencies. For example, the customized sequencing system 104 can utilize statistical inference utilizing the frequency of each of the local nucleotide-base calls, population haplotypes, and frequent variants.

As described above, in some embodiments, the customized sequencing system 104 generates a customized graph reference genome including paths representing the imputed haplotypes for target genomic regions. Accordingly, in one or more embodiments, the customized sequencing system 104 determines the variant-nucleotide-base calls (e.g., SNPs) that surround or flank target genomic regions when initially determining direct nucleotide-base calls and then uses the variant-nucleotide-base calls to impute haplotypes. In some embodiments, the graph reference genome includes imputed haplotypes determined utilizing the variant frequency, local variant-nucleotide-base calls, and the population haplotypes. Rather than use the direct nucleotide-base calls initially determined, when using a customized graph reference genome, the customized sequencing system 104 determines direct nucleotide-base calls based on a comparison of nucleotide-fragment reads from a sample genome with the customized graph reference genome. In such embodiments, the customized sequencing system 104 uses the direct nucleotide-base calls determined with a customized graph reference genome-rather than the direct nucleotide-base calls determined using a linear reference genome or a generic graph reference genomic—as the basis for determining final nucleotide-base calls, as explained below.

In addition to determining the direct nucleotide-base calls 602 and the imputed nucleotide-base calls 606, as further shown in FIG. 6, the customized sequencing system 104 can perform an act 620 of determining final nucleotide-base calls based on the direct nucleotide-base calls 602, the sequencing metrics 604, and the imputed nucleotide-base calls 606. In some cases, for instance, the customized sequencing system 104 weights of a direct nucleotide-base call and an imputed nucleotide-base call for a genomic coordinate at the act 620 and selects either the direct or the imputed nucleotide-base call as the final nucleotide-base call for the genomic coordinate. To illustrate, the customized sequencing system 104 weights the direct nucleotide-base calls 602 based on corresponding data quality and weights imputed nucleotide-base calls 606 based on variant difficulty of the genomic region.

As just suggested, the customized sequencing system 104 can weight a direct nucleotide-base call from the direct nucleotide-base calls 602 based on corresponding sequencing metrics. To illustrate, in some embodiments, the customized sequencing system 104 weights a direct nucleotide-base call based on the quality of the nucleotide-fragment reads used to determine the direct nucleotide-base call and/or the quality of the calling and alignment process utilized to determine the direct nucleotide-base call. For instance, the customized sequencing system 104 can utilize the depth metrics, the read-data-quality metrics, the call-data-quality metrics, and/or the mapping-quality metrics to weight the direct nucleotide-base call. As shown in FIG. 6, the customized sequencing system 104 weights the direct nucleotide-base call proportionally to the quality of the corresponding data. Similarly, the customized sequencing system 104 can weight a direct nucleotide-base call for each genomic coordinate in a genomic region (or for each genomic coordinate in the sample genome) using the method just described.

Further, the customized sequencing system 104 can weight an imputed nucleotide-base call from the imputed nucleotide-base calls 606 based on corresponding variant confidence difficulty. In one or more embodiments, the customized sequencing system 104 determines variant "confidence difficulty" corresponding to a genomic coordinate or a genomic region based on one or more of the frequency of variance at the genomic coordinate or genomic region, the likelihood of variants (or variant types) at the genomic coordinate or region, and/or the length of the genomic region. To illustrate, the customized sequencing system 104 is less likely to correctly impute a nucleotide-base call in a genomic region or coordinate with relatively more frequent variation as measured by allele frequency, at the genomic coordinate or region with a relatively higher degree of variety of variants (or variant types) as represented by haplotypes at the genomic coordinate or region, and/or a relatively large genomic region. An imputed nucleotide-base call for such a genomic coordinate or region would exhibit a relatively higher variant confidence difficulty. Accordingly, in some embodiments, the customized sequencing system 104 weights an imputed nucleotide-base call inversely proportional to variant confidence difficulty corresponding to the genomic coordinate or region. Similarly, the customized sequencing system 104 can weight an imputed nucleotide-base call for each genomic coordinate in a genomic region (or for each genomic coordinate in the sample genome) using the method just described.

In some embodiments, the customized sequencing system 104 determines a final nucleotide-base call for each genomic coordinate of a target genomic region by weighting a direct nucleotide-base call and an imputed nucleotide-base call for each coordinate. For example, in some cases, the customized sequencing system 104 determines a direct nucleotide-base call corresponding to relatively high data quality and relatively high variant confidence difficulty for a genomic coordinate. For such an example, the customized sequencing system 104 is likely to select the direct nucleotide-base call corresponding to high data quality as the final nucleotide-base call for the genomic coordinate, rather than the imputed nucleotide-base call corresponding to high variant confidence difficulty.

In another example, the customized sequencing system 104 determines a direct nucleotide-base call for a genomic coordinate corresponding to relatively low data quality and relatively low variant difficulty. For this example, the customized sequencing system 104 is likely to select the imputed nucleotide-base call corresponding to a low variant difficulty as the final nucleotide-base call rather than the direct nucleotide-base call corresponding to sequencing metrics indicating low data quality.

In some embodiments, the customized sequencing system 104 can implement a threshold for sequencing metrics that, if not satisfied, will lead to automatic selection of the imputed nucleotide-base call for the genomic coordinate. To illustrate, in these embodiments, the customized sequencing system 104 requires a minimum data quality for any potential selection of the direct nucleotide-base call. For example, the customized sequencing system 104 can determine and utilize a minimum Q score or a minimum MAPQ.

Figure 7A:
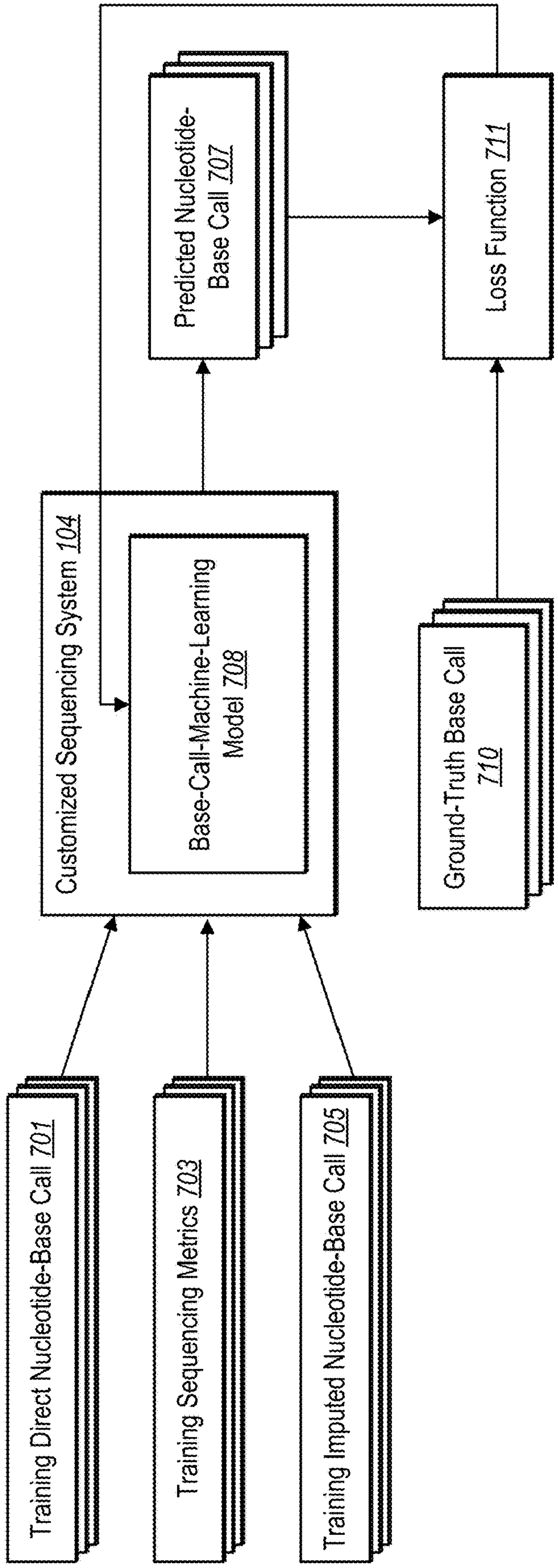
FIGS. 7A-7B illustrate the customized sequencing system training and utilizing a base-call-machine-learning model in accordance with one or more embodiments.
Figure 7B:
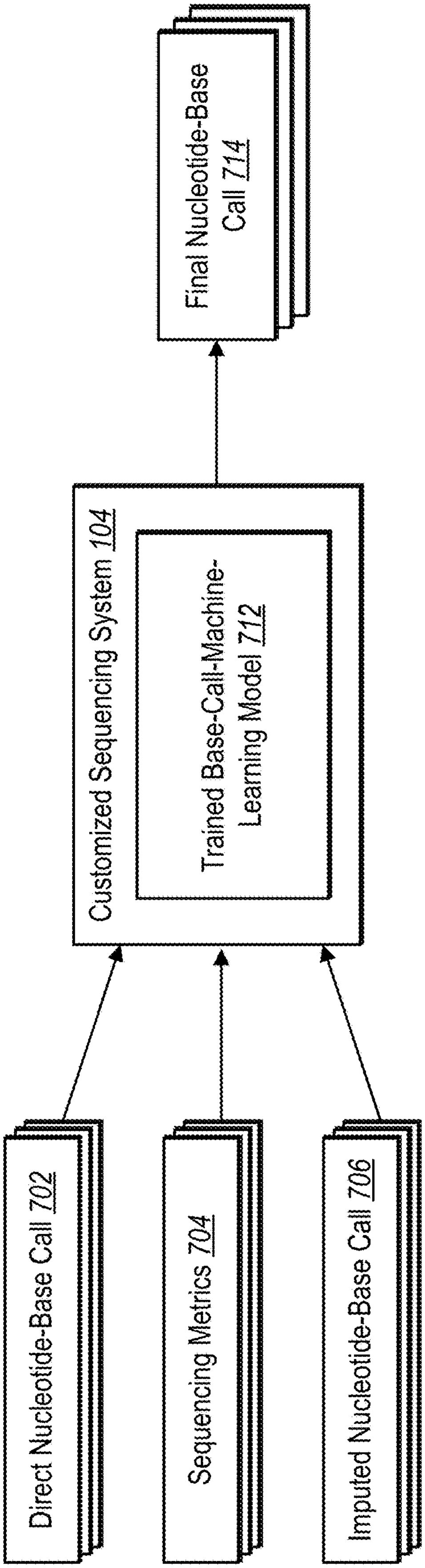

In addition to a weighted model, in one or more embodiments, the customized sequencing system 104 can utilize a machine learning model to determine final nucleotide-base calls. FIGS. 7A-7B illustrate, respectively, training and application of a base-call-machine-learning model to determine final nucleotide-base calls. More specifically, FIGS. 7A-7B illustrate training and applying a machine learning model to determine final nucleotide-base calls based on direct nucleotide-base calls, sequencing metrics, and imputed nucleotide-base calls.

As an overview of the training in FIG. 7A, the customized sequencing system 104 can iteratively input into the base-call-machine-learning model 708: a training direct nucleotide-base call, training sequencing metrics corresponding to the training direct nucleotide-base call, and a training imputed nucleotide-base call for a genomic coordinate. Based on the training data, the base-call-machine-learning model generates a predicted nucleotide-base call for the genomic coordinate in each training iteration, such as by selecting either the direct nucleotide-base call or the imputed nucleotide-base call for the genomic coordinate. The customized sequencing system 104 subsequently compares the predicted nucleotide-base call to a ground-truth base call for the genomic coordinate to determine a loss and adjusts the base-call-machine-learning model based on the loss.

As shown in FIG. 7A, the customized sequencing system 104 receives a training direct nucleotide-base call 701 for a genomic coordinate, training sequencing metrics 703 corresponding to the training direct nucleotide-base call 701, and a training imputed nucleotide-base call 705 for the genomic coordinate. For example, the customized sequencing system 104 can utilize types of sequencing metrics discussed above with regard to FIG. 6, including depth metrics, read-data-quality metrics, call-data-quality metrics, and/or mapping quality metrics.

As further shown in FIG. 7A, the customized sequencing system 104 provides the training direct nucleotide-base call 701, the training sequencing metrics 703, and the training imputed nucleotide-base call 705 to the base-call-machine-learning model 708. Based on the input calls and metrics, as shown in FIG. 7A, the base-call-machine-learning model generates a predicted nucleotide-base call 707 for the genomic coordinate. In some cases, for instance, the base-call-machine-learning model selects either the training direct nucleotide-base call 701 or the training imputed nucleotide-base call 705 as the predicted nucleotide-base call 707. To select either the training direct nucleotide-base call 701 or the training imputed nucleotide-base call 705, in some embodiments, the base-call-machine-learning model 708 can weight a training direct nucleotide-base call differently than a training imputed nucleotide-base call for a genomic coordinate.

As further shown in FIG. 7A, the customized sequencing system 104 compares the predicted nucleotide-base call 707 for the genomic coordinate to a ground-truth base call 710 for the genomic coordinate. In one or more embodiments, the customized sequencing system 104 utilizes a loss function 711 to compare the predicted nucleotide-base call 707 to the ground-truth base call 710. By using the loss function 711, the customized sequencing system 104 determines a difference or a loss between the predicted nucleotide-base call 707 and the ground-truth base call 710. In some embodiments, the customized sequencing system 104 can back-propagate the loss to adjust one or more weights within the base-call-machine-learning model 708.

As further suggested by FIG. 7A, the customized sequencing system 104 can run training iterations. To illustrate, the customized sequencing system 104 can adjust weights for the base-call-machine-learning model 708 iteratively based on comparisons of the predicted nucleotide-base calls to the ground-truth base calls for each genomic coordinate utilizing the loss function 711. After adjustment, the base-call-machine-learning model 708 can generate improve predicted nucleotide-base calls. In some cases, the customized sequencing system 104 runs training iterations until the customized sequencing system 104 determines that a subsequent loss from the loss function 711 is within a minimum threshold or a threshold number of training iterations is reached.

The base-call-machine-learning model 708 can take a variety of forms. For example, in one or more embodiments, the base-call-machine-learning model 708 can include various types of decision trees, support vector machines (SVM), Bayesian networks, or neural networks, such as a convolutional neural network (CNN). In some embodiments, the customized sequencing system 104 utilizes a convolutional deep neural network or a recurrent neural network with many layers as the base-call-machine-learning model 708. In embodiments where the base-call-machine-learning model 708 is a neural network, the customized sequencing system 104 can utilize a cross entropy loss function, an L1 loss function, or a mean squared error loss function as the loss function 711. In one or more additional embodiments, the customized sequencing system 104 utilizes a random forest model, a multilayer perceptron, or a linear regression, a deep tabular learning architecture, a deep learning transformer (e.g., self-attention-based-tabular transformer), or a logistic regression as the base-call-machine-learning model 708.

In addition to the forms identified above, in some cases, the base-call-machine-learning model 708 includes an ensemble of gradient boosted trees. As for the latter embodiment of gradient boosted trees, the customized sequencing system 104 can utilize a mean squared error loss function (e.g., for regression) as the loss function 711. In addition, or in the alternative, the customized sequencing system 104 can utilize a logarithmic loss function (e.g., for classification) as the loss function 711. In some embodiments, the customized sequencing system 104 performs modifications or adjustments to the base-call-machine-learning model 708 to reduce the measure of loss from the loss function 711 for a subsequent training iteration.

For gradient boosted trees, for example, the customized sequencing system 104 trains the base-call-machine-learning model 708 on the gradients of the errors determined by the loss function 711. For instance, the customized sequencing system 104 solves a convex optimization problem (e.g., of infinite dimensions) while regularizing the objective to avoid overfitting. In certain implementations, the customized sequencing system 104 scales the gradients to emphasize corrections to under-represented classes (e.g., where there are significantly more imputed nucleotide-base calls than direct nucleotide-base calls).

In some embodiments, the customized sequencing system 104 adds a new weak learner (e.g., a new boosted tree) to the base-call-machine-learning model 708 for each successive training iteration as part of solving the optimization problem. For example, the customized sequencing system 104 finds a feature (e.g., a sequencing metric) that minimizes a loss from the loss function 711 and either adds the feature to the current iteration's tree or starts to build a new tree with the feature.

In addition to training or without training, in some embodiments, the customized sequencing system 104 applies a trained version of the base-call-machine-learning model 708. FIG. 7B illustrates the customized sequencing system 104 applying a trained base-call-machine-learning model 712 to determine final nucleotide-base calls 714 for genomic coordinates. As depicted in FIG. 7B, the customized sequencing system 104 inputs into the trained base-call-machine-learning model 712: a direct nucleotide-base call 702 for a genomic coordinate, sequencing metrics 704 corresponding to the direct nucleotide-base call 702, and an imputed nucleotide-base call 706 for the genomic coordinate. Based on the direct nucleotide-base call 702, the sequencing metrics 704, and the imputed nucleotide-base call 706, the trained base-call-machine-learning model 712 generates a final nucleotide-base call 714 for the genomic coordinate. To select either the direct nucleotide-base call 702 or the imputed nucleotide-base call 706, in some embodiments, the trained base-call-machine-learning model 712 can weight a direct nucleotide-base call differently than an imputed nucleotide-base call for a genomic coordinate.

As further shown in FIG. 7B, in one or more embodiments, the customized sequencing system 104 system can use the trained base-call-machine-learning model 712 to determine a final nucleotide-base call for each genomic coordinate within one or more target genomic regions of a sample genome or for each genomic coordinate within a sample genome. To illustrate, the customized sequencing system 104 can utilize the trained base-call-machine-learning model 712 to select from among an imputed nucleotide-base call and a direct nucleotide-base call for each genomic coordinate in a genomic region. Additionally, in one or more embodiments, the customized sequencing system 104 utilizes the trained base-call-machine-learning model 712 to determine a final base call for each genomic coordinate of an entire sample genome.

Figure 8:
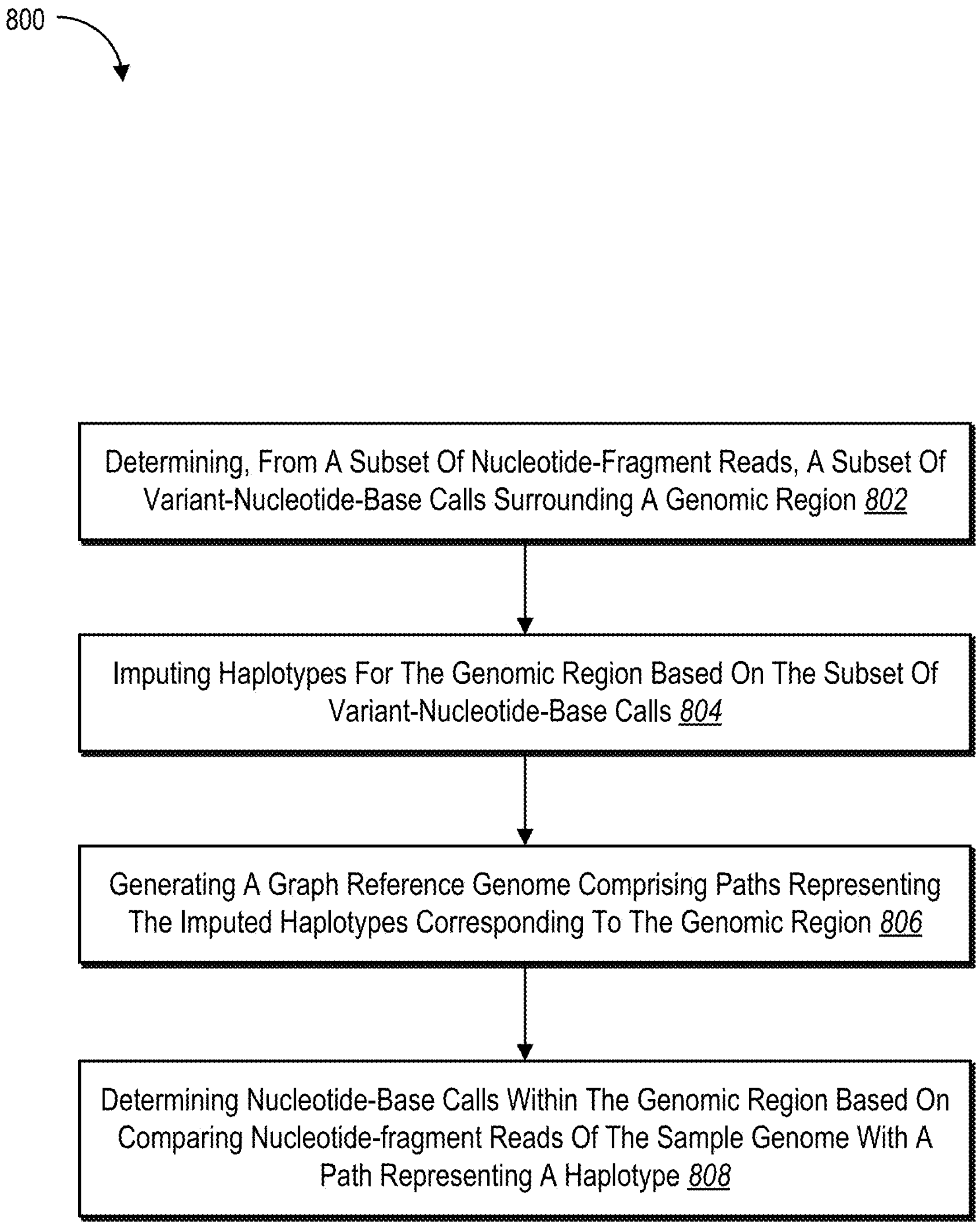
FIG. 8 illustrates a flowchart of a series of acts for generating and utilizing a graph reference genome in accordance with one or more embodiments.
Figure 9:
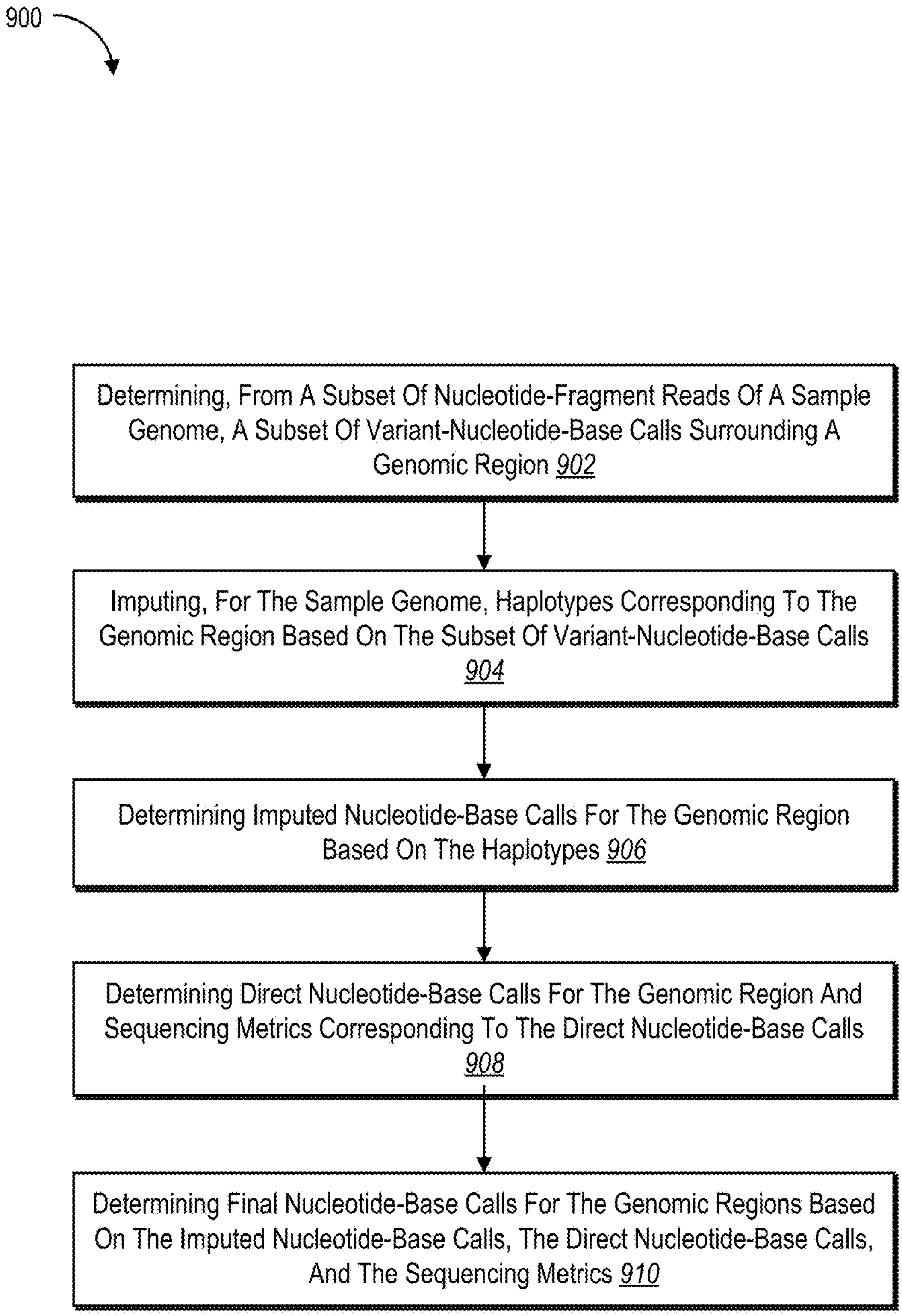
FIGS. 9-10 illustrate flowcharts of series of acts for determining final nucleotide-base calls based on imputed nucleotide-base calls, direct nucleotide-base calls, and sequencing metrics in accordance with one or more embodiments.
Figure 10:
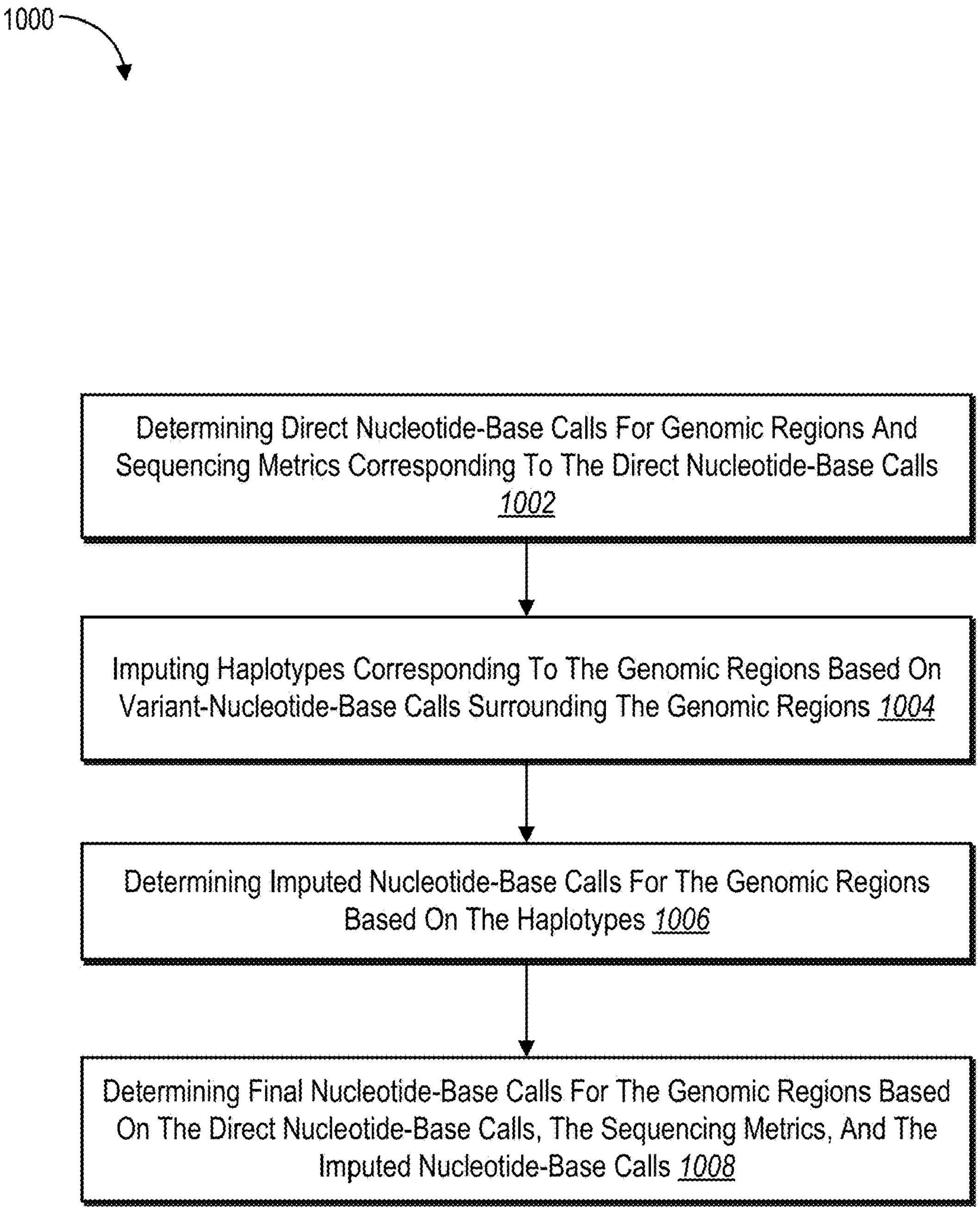

FIGS. 1-7B, the corresponding text, and the examples provide a number of different methods, systems, devices, and non-transitory computer-readable media of the sequencing system. In addition to the foregoing, one or more embodiments can also be described in terms of flowcharts comprising acts for accomplishing a particular result, as shown in FIGS. 8-10. FIGS. 8-10 may be performed with more or fewer acts. Further, the acts may be performed in differing orders. Additionally, the acts described herein may be repeated or performed in parallel with one another or parallel with different instances of the same or similar acts.

As mentioned, FIG. 8 illustrates a flowchart of a series of acts 800 for determining nucleotide-base calls based on comparing nucleotide-fragment reads with a graph reference genome in accordance with one or more embodiments. While FIG. 8 illustrates acts according to one embodiment, alternative embodiments may omit, add to, reorder, and/or modify any of the acts shown in FIG. 8. The acts of FIG. 8 can be performed as part of a method. Alternatively, a non-transitory computer-readable medium can comprise instructions that, when executed by one or more processors, cause a computing device to perform the acts of FIG. 8. In some embodiments, a system can perform the acts of FIG. 8.

As shown in FIG. 8, the series of acts 800 includes an act 802 for determining, from a subset of nucleotide-fragment reads, a subset of variant nucleotide-base calls surrounding a genomic region. In particular, the act 802 can include determining, from a subset of nucleotide-fragment reads of a sample genome, a subset of variant-nucleotide-base calls surrounding a genomic region within the sample genome. Specifically, the act 802 can include determining quality metrics for a subset of nucleotide-base calls within the genomic region do not satisfy a quality-metric threshold and identifying the genomic region as a low-confidence-call region based on the quality metrics for the subset of nucleotide-base calls not satisfying the quality-metric threshold. Further, the act 802 can include wherein the genomic region comprises at least part of a variable number tandem repeat (VNTR), a structural variant, an insertion, or a deletion. As indicated above, when performing the act 802, determining the subset of variant nucleotide-base calls surrounding the genomic region can be based on a subset of nucleotide-fragment reads from the initial fifty base pairs of a 2×150 sequencing run or at approximately 1× read depth.

Additionally, the series of acts 800 includes an act 804 for imputing haplotypes for the genomic region based on the subset of variant nucleotide-base calls. In particular, the act 804 can include impute haplotypes for the genomic region corresponding to the sample genome based on the subset of variant-nucleotide-base calls. Specifically, the act 804 can include determining the subset of variant-nucleotide-base calls surrounding the genomic region by determining single-nucleotide polymorphisms (SNPs) surrounding the genomic region, and imputing the haplotypes for the genomic region by imputing the haplotypes corresponding to the sample genome based on the SNPs. Also, in one or more embodiments, the act 804 includes imputing the haplotypes for the genomic region from a haplotype database of population haplotypes.

Further, the series of acts 800 includes an act 806 for generating a graph reference genome comprising paths representing the imputed haplotypes corresponding to the genomic region. In particular, the act 806 can include generate, for the sample genome, a graph reference genome comprising paths representing the imputed haplotypes corresponding to the genomic region. Specifically, the act 806 can include determining a variant-nucleotide-base call corresponding to an additional genomic region within the sample genome, determining additional imputed haplotypes for the additional genomic region based on the variant-nucleotide-base call; and generating the graph reference genome comprising an additional path representing the additional imputed haplotypes. Additionally, the act 806 can include determine genomic coordinates for the genomic region from a linear reference genome, and generating the graph reference genome comprising the linear reference genome and the paths representing the imputed haplotypes corresponding to the genomic region located at the genomic coordinates of the linear reference genome.

Also, the series of acts 800 includes an act 808 for determining nucleotide-base call within the genomic region based on comparing nucleotide-fragment reads of the sample genome with a path representing a haplotype. In particular, the act 808 can include determining nucleotide-base calls within the genomic region for the sample genome based on comparing nucleotide-fragment reads of the sample genome with a path representing an imputed haplotype within the graph reference genome. For instance, the act 808 can include determining nucleotide-base calls within the genomic region for the sample genome based on aligning nucleotide-fragment reads of the sample genome with a path representing an imputed haplotype within the graph reference genome. Specifically, the act 808 can include determining a direct nucleotide-base call for a genomic coordinate within the genomic region based on a comparison of the nucleotide-fragment reads of the sample genome with the path representing the imputed haplotype, determining an imputed nucleotide-base call for the genomic coordinate within the genomic region based on the imputed haplotypes for the genomic region, and determining a final nucleotide-base call for the genomic coordinate within the genomic region based on the direct nucleotide-base call and the imputed nucleotide-base call.

Further, the act 808 can include determining sequencing metrics corresponding to the direct nucleotide-base call for the genomic coordinate, and determining the final nucleotide-base call for the genomic coordinate by assigning a first weight to the direct nucleotide-base call and a second weight to the imputed nucleotide-base call based on the sequencing metrics and variability of the genomic region.

As mentioned, FIG. 9 illustrates a flowchart of a series of acts 900 for determining nucleotide-base calls based on imputed nucleotide-base calls, direct nucleotide-base calls, and sequencing metrics in accordance with one or more embodiments. While FIG. 9 illustrates acts according to one embodiment, alternative embodiments may omit, add to, reorder, and/or modify any of the acts shown in FIG. 9. The acts of FIG. 9 can be performed as part of a method. Alternatively, a non-transitory computer-readable medium can comprise instructions that, when executed by one or more processors, cause a computing device to perform the acts of FIG. 9. In some embodiments, a system can perform the acts of FIG. 9.

As shown in FIG. 9, the series of acts 900 includes an act 902 for determining, from a subset of nucleotide-fragment reads of a sample genome, a subset of variant nucleotide-base calls surrounding a genomic region. In particular, the act 902 can include determining, from a subset of nucleotide-fragment reads of a sample genome, a subset of variant-nucleotide-base calls surrounding a genomic region within the sample genome. As indicated above, when performing the act 902, determining the subset of variant nucleotide-base calls surrounding the genomic region can be based on a subset of nucleotide-fragment reads from the initial thirty-five base pairs, initial fifty base pairs, initial seventy-five base pairs, or other initial number of base pairs of a 2×150 sequencing run or at approximately 1× read depth.

As shown in FIG. 9, the series of acts 900 includes an act 904 for imputing, for the sample genome, haplotypes corresponding to the genomic region based on the subset of variant nucleotide-base call calls. In particular, the act 904 can include imputing, for the sample genome, haplotypes corresponding to the genomic region based on the subset of variant-nucleotide-base calls.

As shown in FIG. 9, the series of acts 900 includes an act 906 for determining imputed nucleotide-base calls for the genomic region based on the haplotypes. In particular, the act 906 can include determining, for the sample genome, imputed nucleotide-base calls for the genomic region based on the imputed haplotypes.

As shown in FIG. 9, the series of acts 900 includes an act 908 for determining direct nucleotide-base calls for the genomic region and sequencing metrics corresponding to the direct nucleotide-base calls. In particular, the act 908 can include determining, for the sample genome, direct nucleotide-base calls for the genomic region and sequencing metrics corresponding to the direct nucleotide-base calls. Specifically, the act 908 can include determining the sequencing metrics corresponding to the direct nucleotide-base calls by determining depth metrics, read-data-quality metrics, call-data-quality metrics, or mapping-quality metrics for the direct nucleotide-base calls.

As shown in FIG. 9, the series of acts 900 includes an act 910 for determining final nucleotide-base calls for the genomic regions based on the imputed nucleotide-base calls, the direct nucleotide-base calls, and the sequencing metrics. In particular, the act 910 can include determining final nucleotide-base calls for the genomic region based on the imputed nucleotide-base calls, the direct nucleotide-base calls, and the sequencing metrics. Specifically, the act 910 can include determining, from a subset of nucleotide-fragment reads of a sample genome, a subset of variant-nucleotide-base calls surrounding a genomic region within the sample genome, imputing, for the sample genome, haplotypes corresponding to the genomic region based on the subset of variant-nucleotide-base calls, determining, for the sample genome, imputed nucleotide-base calls for the genomic region based on the imputed haplotypes, determining, for the sample genome, direct nucleotide-base calls for the genomic region and sequencing metrics corresponding to the direct nucleotide-base calls, and determining final nucleotide-base calls for the genomic region based on the imputed nucleotide-base calls, the direct nucleotide-base calls, and the sequencing metrics.

Additionally, the act 910 can include determine the final nucleotide-base calls for the genomic region by utilizing a base-call-machine-learning model to determine the final nucleotide-base calls based on the imputed nucleotide-base calls, the direct nucleotide-base calls, and the sequencing metrics. Further, the act 910 can include determining the final nucleotide-base calls for the genomic region by weighting one or more of the direct nucleotide-base calls differently than one or more of the imputed nucleotide-base calls based on variability of the genomic region and one or more of the sequencing metrics corresponding to the direct nucleotide-base calls. Also, the act 910 can include wherein the variability of the genomic region comprises genotype variability of the genomic region and length of the genomic region, and one or more of the sequencing metrics comprise read-data-quality metrics or mapping-quality metrics for the direct nucleotide-base calls corresponding to nucleotide-fragment reads and call-data-quality metrics for the direct nucleotide-base calls corresponding to the nucleotide-fragment reads.

In one or more embodiments, the series of acts 900 can include generating, for the sample genome, a graph reference genome comprising a linear reference genome and paths representing the imputed haplotypes corresponding to the genomic region, and determining a direct variant-nucleotide-base call for a genomic coordinate inside or outside of the genomic region based on identifying an inconsistency between nucleotide-base-fragment reads corresponding to the genomic coordinate and a corresponding nucleotide base at the genomic coordinate within the linear reference genome. Also, the series of acts 900 can include generating, for the sample genome, a graph reference genome comprising paths representing the imputed haplotypes corresponding to the genomic region, and determining the direct nucleotide-base calls for the genomic region based on comparing nucleotide-fragment reads of the sample genome with a path representing an imputed haplotype within the graph reference genome. In particular, comparing nucleotide-fragment reads of the sample genome with the path can include aligning the nucleotide-fragment reads of the sample genome with the path representing the imputed haplotype within the graph reference genome.

Additionally, in one or more embodiments, the series of acts 900 includes determining the direct nucleotide-base calls by determining nucleotide-base calls based on a first subset of nucleotide-fragment reads from the sample genome aligned with a linear reference genome within a graph reference genome, and determining nucleotide-base calls based on a second subset of nucleotide-fragment reads from the sample genome aligned with paths representing one or more imputed haplotypes from the graph reference genome.

As mentioned, FIG. 10 illustrates a flowchart of a series of acts 1000 for determining nucleotide-base calls based on direct nucleotide-base calls, sequencing metrics, and imputed nucleotide-base calls in accordance with one or more embodiments. While FIG. 10 illustrates acts according to one embodiment, alternative embodiments may omit, add to, reorder, and/or modify any of the acts shown in FIG. 10. The acts of FIG. 10 can be performed as part of a method. Alternatively, a non-transitory computer-readable medium can comprise instructions that, when executed by one or more processors, cause a computing device to perform the acts of FIG. 10. In some embodiments, a system can perform the acts of FIG. 10.

As shown in FIG. 10, the series of acts 1000 includes an act 1002 for determining direct nucleotide-base calls for genomic regions and sequencing metrics corresponding to the direct nucleotide-base calls. In particular, the act 1002 can include determining, for a sample genome, direct nucleotide-base calls for genomic regions and sequencing metrics corresponding to the direct nucleotide-base calls. Determining the direct nucleotide-base calls can include determining direct nucleotide-base calls based on an alignment between nucleotide-fragment reads from the sample genome and a reference genome. Specifically, the act 1002 can include determining the sequencing metrics corresponding to the direct nucleotide-base calls by determining depth metrics, read-data-quality metrics, call-data-quality metrics, or mapping-quality metrics for the direct nucleotide-base calls.

As shown in FIG. 10, the series of acts 1000 includes an act 1004 for imputing haplotypes corresponding to the genomic regions based on variant nucleotide-base calls surrounding the genomic regions. In particular, the act 1004 can include imputing, for the sample genome, haplotypes corresponding to the genomic regions based on variant-nucleotide-base calls surrounding the genomic regions.

As shown in FIG. 10, the series of acts 1000 includes an act 1006 for determining imputed nucleotide-base calls for the genomic regions based on the haplotypes. In particular, the act 1006 can include determining, for the sample genome, imputed nucleotide-base calls for the genomic regions based on the imputed haplotypes.

As shown in FIG. 10, the series of acts 1000 includes an act 1008 for determining final nucleotide-base calls for the genomic regions based on the direct nucleotide-base calls, the sequencing metrics, and the imputed nucleotide-base calls. In particular, the act 1008 can include determining final nucleotide-base calls for the genomic regions based on the direct nucleotide-base calls, the sequencing metrics, and the imputed nucleotide-base calls. Specifically, the act 1008 can include utilizing a base-call-machine-learning model to determine the final nucleotide-base calls based on the imputed nucleotide-base calls, the direct nucleotide-base calls, and the sequencing metrics.

Additionally, the act 1008 can include determining the final nucleotide-base calls for the genomic regions comprises weighting a direct nucleotide-base call differently than an imputed nucleotide-base call based on genotype variability of a genomic coordinate for the direct nucleotide-base call and one or more of read-data-quality metrics for the direct nucleotide-base call corresponding to nucleotide-fragment reads or call-data-quality metrics for the direct nucleotide-base call corresponding to the nucleotide-fragment reads. Further, the act 1008 can include utilizing a base-call-machine-learning model to weight a direct nucleotide-base call differently than an imputed nucleotide-base call for a genomic coordinate, and select one of the direct nucleotide-base call or the imputed nucleotide-base call as a final nucleotide-base call for the genomic coordinate.

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid (i.e., a nucleic-acid polymer) can be an automated process. Preferred embodiments include sequencing-by-synthesis (SBS) techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed, and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments, each image will show nucleic acid features that have incorporated nucleotides of a particular type. Different features are present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102:5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features are present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666, which is incorporated herein by reference.

The sequencing system described above sequences nucleic-acid polymers present in samples received by a sequencing device. As defined herein, "sample" and its derivatives, is used in its broadest sense and includes any specimen, culture and the like that is suspected of including a target. In some embodiments, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

The nucleic acid sample can include high molecular weight material such as genomic DNA (gDNA). The sample can include low molecular weight material such as nucleic acid molecules obtained from FFPE or archived DNA samples. In another embodiment, low molecular weight material includes enzymatically or mechanically fragmented DNA. The sample can include cell-free circulating DNA. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude DNA containing lysate, for example derived from a buccal swab, paper, fabric or other substrate that may be impregnated with saliva, blood, or other bodily fluids. As such, in some embodiments, the nucleic acid sample may comprise low amounts of, or fragmented portions of DNA, such as genomic DNA. In some embodiments, target sequences can be present in one or more bodily fluids including but not limited to, blood, sputum, plasma, semen, urine and serum. In some embodiments, target sequences can be obtained from hair, skin, tissue samples, autopsy or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences or amplified target sequences are directed to purposes of human identification. In some embodiments, the disclosure relates generally to methods for identifying characteristics of a forensic sample. In some embodiments, the disclosure relates generally to human identification methods using one or more target specific primers disclosed herein or one or more target specific primers designed using the primer design criteria outlined herein. In one embodiment, a forensic or human identification sample containing at least one target sequence can be amplified using any one or more of the target-specific primers disclosed herein or using the primer criteria outlined herein.

The components of the customized sequencing system 104 can include software, hardware, or both. For example, the components of the customized sequencing system 104 can include one or more instructions stored on a computer-readable storage medium and executable by processors of one or more computing devices (e.g., the user client device 108). When executed by the one or more processors, the computer-executable instructions of the customized sequencing system 104 can cause the computing devices to perform the bubble detection methods described herein. Alternatively, the components of the customized sequencing system 104 can comprise hardware, such as special purpose processing devices to perform a certain function or group of functions. Additionally, or alternatively, the components of the customized sequencing system 104 can include a combination of computer-executable instructions and hardware.

Furthermore, the components of the customized sequencing system 104 performing the functions described herein with respect to the customized sequencing system 104 may, for example, be implemented as part of a stand-alone application, as a module of an application, as a plug-in for applications, as a library function or functions that may be called by other applications, and/or as a cloud-computing model. Thus, components of the customized sequencing system 104 may be implemented as part of a stand-alone application on a personal computing device or a mobile device. Additionally, or alternatively, the components of the customized sequencing system 104 may be implemented in any application that provides sequencing services including, but not limited to Illumina BaseSpace, Illumina DRAGEN, or Illumina TruSight software. "Illumina," "BaseSpace," "DRAGEN," and "TruSight," are either registered trademarks or trademarks of Illumina, Inc. in the United States and/or other countries.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives (SSDs) (e.g., based on RAM), Flash memory, phase-change memory (PCM), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a NIC), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. In some embodiments, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service (SaaS), Platform as a Service (PaaS), and Infrastructure as a Service (IaaS). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 11:
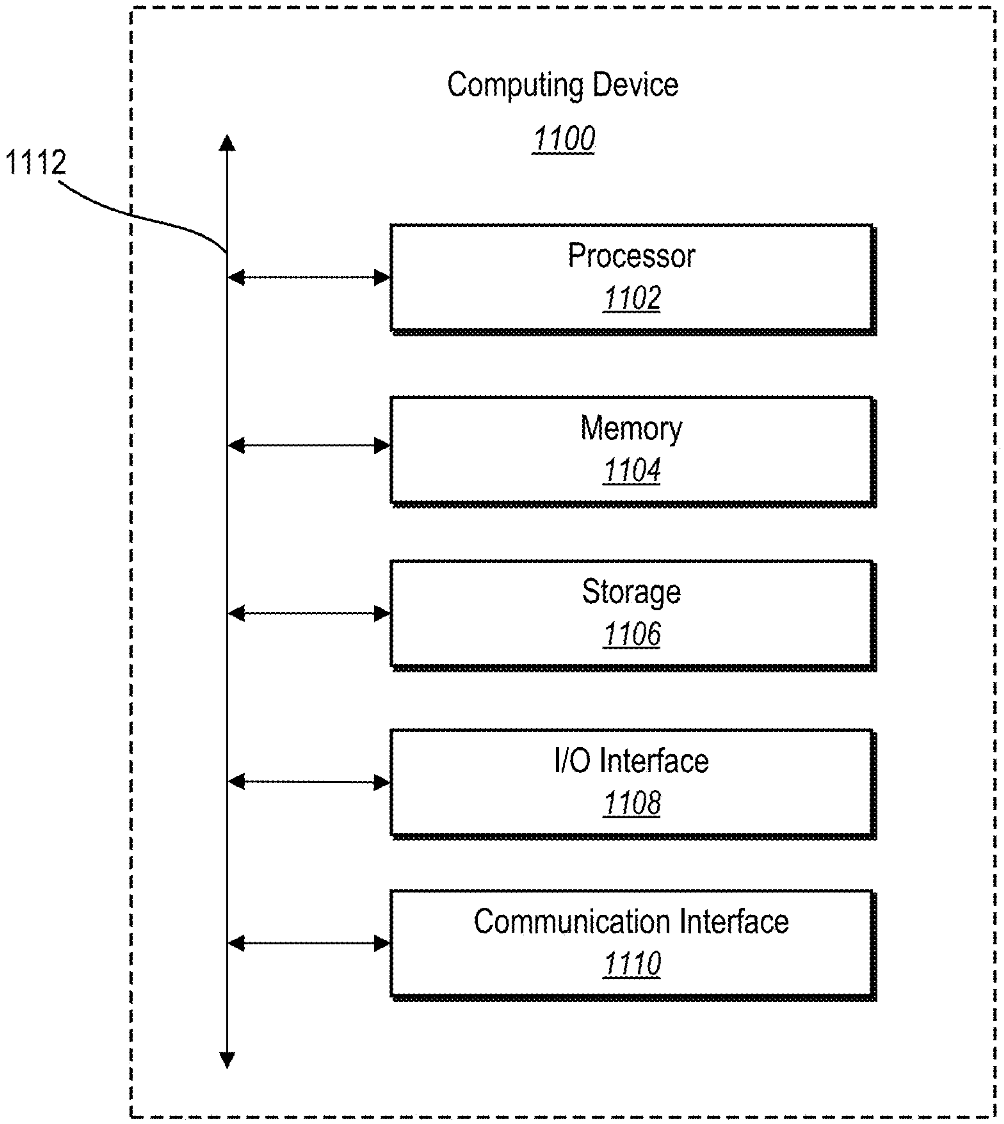
FIG. 11 illustrates a block diagram of an example computing device for implementing one or more embodiments of the present disclosure.

FIG. 11 illustrates a block diagram of a computing device 1100 that may be configured to perform one or more of the processes described above. One will appreciate that one or more computing devices such as the computing device 1100 may implement the customized sequencing system 104. As shown by FIG. 11, the computing device 1100 can comprise a processor 1102, a memory 1104, a storage device 1106, an I/O interface 1108, and a communication interface 1110, which may be communicatively coupled by way of a communication infrastructure 1112. In certain embodiments, the computing device 1100 can include fewer or more components than those shown in FIG. 11. The following paragraphs describe components of the computing device 1100 shown in FIG. 11 in additional detail.

In one or more embodiments, the processor 1102 includes hardware for executing instructions, such as those making up a computer program. As an example, and not by way of limitation, to execute instructions for dynamically modifying workflows, the processor 1102 may retrieve (or fetch) the instructions from an internal register, an internal cache, the memory 1104, or the storage device 1106 and decode and execute them. The memory 1104 may be a volatile or non-volatile memory used for storing data, metadata, and programs for execution by the processor(s). The storage device 1106 includes storage, such as a hard disk, flash disk drive, or other digital storage device, for storing data or instructions for performing the methods described herein.

The I/O interface 1108 allows a user to provide input to, receive output from, and otherwise transfer data to and receive data from computing device 1100. The I/O interface 1108 may include a mouse, a keypad or a keyboard, a touch screen, a camera, an optical scanner, network interface, modem, other known I/O devices or a combination of such I/O interfaces. The I/O interface 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 1108 is configured to provide graphical data to a display for presentation to a user. The graphical data may be representative of one or more graphical user interfaces and/or any other graphical content as may serve a particular implementation.

The communication interface 1110 can include hardware, software, or both. In any event, the communication interface 1110 can provide one or more interfaces for communication (such as, for example, packet-based communication) between the computing device 1100 and one or more other computing devices or networks. As an example, and not by way of limitation, the communication interface 1110 may include a network interface controller (NIC) or network adapter for communicating with an Ethernet or other wire-based network or a wireless NIC (WNIC) or wireless adapter for communicating with a wireless network, such as a WI-FI.

Additionally, the communication interface 1110 may facilitate communications with various types of wired or wireless networks. The communication interface 1110 may also facilitate communications using various communication protocols. The communication infrastructure 1112 may also include hardware, software, or both that couples components of the computing device 1100 to each other. For example, the communication interface 1110 may use one or more networks and/or protocols to enable a plurality of computing devices connected by a particular infrastructure to communicate with each other to perform one or more aspects of the processes described herein. To illustrate, the sequencing process can allow a plurality of devices (e.g., a client device, sequencing device, and server device(s)) to exchange information such as sequencing data and error notifications.

In the foregoing specification, the present disclosure has been described with reference to specific exemplary embodiments thereof. Various embodiments and aspects of the present disclosure(s) are described with reference to details discussed herein, and the accompanying drawings illustrate the various embodiments. The description above and drawings are illustrative of the disclosure and are not to be construed as limiting the disclosure. Numerous specific details are described to provide a thorough understanding of various embodiments of the present disclosure.

The present disclosure may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel with one another or in parallel with different instances of the same or similar steps/acts. The scope of the present application is, therefore, indicated by the appended claims rather than by the foregoing description. All changes that come within the meaning and range of equivalency of the claims are to be embraced within their scope.

What is claimed is:

1. A system comprising:

at least one processor; and a non-transitory computer readable medium comprising instructions that, when executed by the at least one processor, cause the system to:

align a subset of nucleotide-fragment reads of a sample genome with a reference genome;

determine, from a comparison of the aligned subset of nucleotide-fragment reads of the sample genome with the reference genome, a subset of variant-nucleotide-base calls surrounding a genomic region within the sample genome;

impute haplotypes for the genomic region corresponding to the sample genome based on the subset of variant-nucleotide-base calls;

generate, for the sample genome, a customized graph reference genome comprising paths representing portions of the reference genome and paths representing the imputed haplotypes corresponding to the genomic region within the sample genome; and determine final variant-nucleotide-base calls within the genomic region for the sample genome based on comparing one or more nucleotide-fragment reads of the sample genome with a path representing an imputed haplotype within the customized graph reference genome.

2. The system of claim 1, further comprising instructions that, when executed by the at least one processor, cause the system to:

determine the subset of variant-nucleotide-base calls surrounding the genomic region by determining single-nucleotide polymorphisms (SNPs) surrounding the genomic region; and impute the haplotypes for the genomic region by imputing the haplotypes corresponding to the sample genome based on the SNPs.

3. The system of claim 1, further comprising instructions that, when executed by the at least one processor, cause the system to impute the haplotypes for the genomic region from a haplotype database of population haplotypes.

4. The system of claim 1, further comprising instructions that, when executed by the at least one processor, cause the system to:

determine a variant-nucleotide-base call corresponding to an additional genomic region within the sample genome;

determine additional imputed haplotypes for the additional genomic region based on the variant-nucleotide-base call; and generate the customized graph reference genome further comprising an additional path representing the additional imputed haplotypes.

5. The system of claim 1, further comprising instructions that, when executed by the at least one processor, cause the system to:

determine quality metrics for a subset of nucleotide-base calls within the genomic region do not satisfy a quality-metric threshold; and identify the genomic region as a low-confidence-call region based on the quality metrics for the subset of nucleotide-base calls not satisfying the quality-metric threshold.

6. The system of claim 1, further comprising instructions that, when executed by the at least one processor, cause the system to:

determine a direct nucleotide-base call for a genomic coordinate within the genomic region based on a comparison of the one or more nucleotide-fragment reads of the sample genome with the path representing the imputed haplotype;

determine an imputed nucleotide-base call for the genomic coordinate within the genomic region based on the imputed haplotypes for the genomic region; and determine a final variant-nucleotide-base call for the genomic coordinate within the genomic region based on the direct nucleotide-base call and the imputed nucleotide-base call.

7. The system of claim 6, further comprising instructions that, when executed by the at least one processor, cause the system to:

determine sequencing metrics corresponding to the direct nucleotide-base call for the genomic coordinate; and determine the final variant-nucleotide-base call for the genomic coordinate by assigning a first weight to the direct nucleotide-base call and a second weight to the imputed nucleotide-base call based on the sequencing metrics and variability of the genomic region.

8. The system of claim 1, wherein the genomic region comprises at least part of a variable number tandem repeat (VNTR), a structural variant, an insertion, or a deletion.

9. The system of claim 1, further comprising instructions that, when executed by the at least one processor, cause the system to:

determine genomic coordinates for the genomic region from a linear reference genome; and generate the customized graph reference genome comprising the paths representing the imputed haplotypes corresponding to the genomic region located at the genomic coordinates of the linear reference genome.

10. A non-transitory computer-readable medium storing instructions that, when executed by at least one processor, cause a computing device to:

align a subset of nucleotide-fragment reads of a sample genome with a reference genome;

determine, from a comparison of the aligned subset of nucleotide-fragment reads of the sample genome with the reference genome, a subset of variant-nucleotide-base calls surrounding a genomic region within the sample genome;

impute, for the sample genome, haplotypes corresponding to the genomic region based on the subset of variant-nucleotide-base calls;

determine, for the sample genome, imputed nucleotide-base calls for the genomic region based on the imputed haplotypes;

access a customized graph reference genome comprising paths representing portions of the reference genome and paths representing the imputed haplotypes corresponding to the genomic region within the sample genome;

determine, for the sample genome and by comparing the aligned subset of nucleotide-fragment reads with the customized graph reference genome, direct nucleotide-base calls for the genomic region and sequencing metrics corresponding to the direct nucleotide-base calls; and determine final variant-nucleotide-base calls for the genomic region by comparing the imputed nucleotide-base calls, and the direct nucleotide-base calls, based on the sequencing metrics.

11. The non-transitory computer-readable medium of claim 10, further comprising instructions that, when executed by the at least one processor, causes the computing device to:

generate, for the sample genome, the customized graph reference genome comprising paths representing portions of the reference genome and paths representing the imputed haplotypes corresponding to the genomic region within the sample genome; and determine the direct nucleotide-base calls for the genomic region based on comparing the aligned subset of nucleotide-fragment reads of the sample genome with a path representing an imputed haplotype within the customized graph reference genome.

12. The non-transitory computer-readable medium of claim 10, further comprising instructions that, when executed by the at least one processor, causes the computing device to:

access the customized graph reference genome comprising the paths representing the portions of the reference genome by accessing the customized graph reference genome comprising a linear reference genome; and determine a direct variant-nucleotide-base call for a genomic coordinate inside or outside of the genomic region based on identifying an inconsistency between one or more nucleotide-base-fragment reads corresponding to the genomic coordinate and a corresponding nucleotide base at the genomic coordinate within the linear reference genome.

13. The non-transitory computer-readable medium of claim 10, further comprising instructions that, when executed by the at least one processor, causes the computing device to determine the direct nucleotide-base calls comprising direct variant-nucleotide-base calls or direct invariant-nucleotide-base calls by:

determining nucleotide-base calls based on a first subset of nucleotide-fragment reads from the sample genome aligned with a linear reference genome within the customized graph reference genome; and determining nucleotide-base calls based on a second subset of nucleotide-fragment reads from the sample genome aligned with the paths representing the imputed haplotypes from the customized graph reference genome.

14. The non-transitory computer-readable medium of claim 10, further comprising instructions that, when executed by the at least one processor, cause the computing device to determine the final variant-nucleotide-base calls for the genomic region by weighting one or more of the direct nucleotide-base calls differently than one or more of the imputed nucleotide-base calls based on variability of the genomic region and one or more of the sequencing metrics corresponding to the direct nucleotide-base calls.

15. The non-transitory computer-readable medium of claim 14, wherein:

the variability of the genomic region comprises genotype variability of the genomic region and length of the genomic region; and one or more of the sequencing metrics comprise read-data-quality metrics or mapping-quality metrics for the direct nucleotide-base calls corresponding to nucleotide-fragment reads and call-data-quality metrics for the direct nucleotide-base calls corresponding to the nucleotide-fragment reads.

16. A computer-implemented method comprising:

aligning nucleotide-fragment reads of a sample genome with a customized graph reference genome comprising paths representing portions of a reference genome and paths representing imputed haplotypes corresponding to a genomic region within the sample genome;

determining, by comparing the aligned nucleotide-fragment reads of the sample genome with a customized graph reference genome, direct nucleotide-base calls for genomic regions and sequencing metrics corresponding to the direct nucleotide-base calls;

imputing, for the sample genome, haplotypes corresponding to the genomic regions based on variant-nucleotide-base calls surrounding the genomic regions;

determining, for the sample genome, imputed nucleotide-base calls for the genomic regions based on the imputed haplotypes; and determining final variant-nucleotide-base calls for the genomic regions by comparing the direct nucleotide-base calls with the imputed nucleotide-base calls based on the sequencing metrics.

17. The computer-implemented method of claim 16, wherein determining the sequencing metrics corresponding to the direct nucleotide-base calls comprises determining depth metrics, read-data-quality metrics, call-data-quality metrics, or mapping-quality metrics for the direct nucleotide-base calls.

18. The computer-implemented method of claim 16, wherein determining the final variant-nucleotide-base calls for the genomic regions comprises utilizing a base-call-machine-learning model to determine the final variant-nucleotide-base calls based on the imputed nucleotide-base calls, the direct nucleotide-base calls, and the sequencing metrics.

19. The computer-implemented method of claim 16, wherein determining the final variant-nucleotide-base calls for the genomic regions comprises weighting a direct nucleotide-base call differently than an imputed nucleotide-base call based on genotype variability of a genomic coordinate for the direct nucleotide-base call and one or more of read-data-quality metrics for the direct nucleotide-base call corresponding to nucleotide-fragment reads or call-data-quality metrics for the direct nucleotide-base call corresponding to the nucleotide-fragment reads.

20. The computer-implemented method of claim 16, wherein determining the final variant-nucleotide-base calls for the genomic regions comprises utilizing a base-call-machine-learning model to:

weight a direct nucleotide-base call differently than an imputed nucleotide-base call for a genomic coordinate; and select one of the direct nucleotide-base call or the imputed nucleotide-base call as a final variant-nucleotide-base call for the genomic coordinate.

* * * * *